United States Patent
Eggers

(10) Patent No.: US 7,828,797 B2
(45) Date of Patent: Nov. 9, 2010

(54) ELECTROSURGICAL ACCESSING OF TISSUE WITH CONTROLLED COLLATERAL THERMAL PHENOMENA

(75) Inventor: Philip E. Eggers, Dublin, OH (US)

(73) Assignee: Intact Medical Corporation, Natick, MA (US)

( * ) Notice: Subject to any disclaimer, the term of this patent is extended or adjusted under 35 U.S.C. 154(b) by 1316 days.

(21) Appl. No.: 11/265,582

(22) Filed: Nov. 2, 2005

(65) Prior Publication Data

US 2006/0095027 A1      May 4, 2006

Related U.S. Application Data

(60) Division of application No. 10/630,100, filed on Jul. 30, 2003, now Pat. No. 7,041,101, which is a continuation-in-part of application No. 10/235,131, filed on Sep. 5, 2002, now abandoned, which is a continuation-in-part of application No. 09/904,396, filed on Jul. 12, 2001, now Pat. No. 6,471,659, which is a continuation-in-part of application No. 09/472,673, filed on Dec. 27, 1999, now Pat. No. 6,277,083.

(51) Int. Cl.
    *A61B 18/14*      (2006.01)
(52) U.S. Cl. .......................................... 606/46; 606/41
(58) Field of Classification Search ............. 606/45–50; 600/564–567
See application file for complete search history.

(56) References Cited

U.S. PATENT DOCUMENTS

| | | | |
|---|---|---|---|
| 3,910,279 A * | 10/1975 | Okada et al. ................... | 606/47 |
| 5,425,731 A | 6/1995 | Daniel et al. | |
| 5,520,685 A | 5/1996 | Wojciechowicz | |
| 5,647,871 A | 7/1997 | Levine et al. | |
| 5,718,709 A | 2/1998 | Considine | |
| 5,730,742 A | 3/1998 | Wojciechowicz | |
| 5,810,806 A * | 9/1998 | Ritchart et al. ................. | 606/45 |
| 5,814,044 A * | 9/1998 | Hooven ........................ | 606/48 |
| 6,022,362 A | 2/2000 | Lee et al. | |
| 6,074,389 A | 6/2000 | Levine et al. | |
| 6,277,083 B1 | 8/2001 | Eggers et al. | |
| 6,296,637 B1 | 10/2001 | Thorne et al. | |
| 6,331,166 B1 * | 12/2001 | Burbank et al. ............. | 600/567 |
| 6,440,147 B1 | 8/2002 | Lee et al. | |
| 6,471,659 B2 | 10/2002 | Eggers et al. | |
| 6,471,700 B1 | 10/2002 | Burbank et al. | |
| 6,514,248 B1 * | 2/2003 | Eggers et al. ................. | 606/41 |

(Continued)

OTHER PUBLICATIONS

Parker, Steve H., "The Advanced Breast Biopsy Instrumentation: Another Trojan Horse?" Am. J. Radiology 171: 51-53 (1998).

(Continued)

*Primary Examiner*—Michael Peffley
(74) *Attorney, Agent, or Firm*—Mueller Smith & Okuley, LLC

(57) ABSTRACT

Method, system and apparatus for carrying out electrosurgical procedures interstitially. Elevated temperature fluid such as steam generated by an instrument born electrosurgical cutting arc is evacuated through an intake port located adjacent the cutting electrode. Instrument cannula surface heating caused by transport of the heated fluid is isolated. Such thermal isolation is provided by a thermal shield which may be configured as an enveloping sheath.

7 Claims, 20 Drawing Sheets

U.S. PATENT DOCUMENTS

| | | |
|---|---|---|
| 6,676,658 B2 * | 1/2004 | Burbank et al. .............. 606/45 |
| 6,702,831 B2 | 3/2004 | Lee et al. |
| 6,764,495 B2 | 7/2004 | Lee et al. |
| 6,780,179 B2 | 8/2004 | Lee et al. |
| 2001/0025179 A1 | 9/2001 | Lee et al. |
| 2002/0015691 A1 | 2/2002 | Levine et al. |
| 2002/0019597 A1 | 2/2002 | Dubrul et al. |
| 2002/0072739 A1 | 6/2002 | Lee et al. |
| 2002/0077648 A1 | 6/2002 | Lee et al. |
| 2002/0095100 A1 | 7/2002 | Lee et al. |
| 2002/0099398 A1 | 7/2002 | Lee et al. |
| 2002/0099399 A1 | 7/2002 | Lee et al. |
| 2002/0111564 A1 | 8/2002 | Burbank et al. |
| 2002/0123762 A1 | 9/2002 | Lee et al. |
| 2002/0193705 A1 | 12/2002 | Burbank et al. |
| 2003/0023239 A1 | 1/2003 | Burbank et al. |
| 2003/0109870 A1 | 6/2003 | Lee et al. |
| 2003/0163129 A1 | 8/2003 | Lee et al. |
| 2003/0220640 A1 | 11/2003 | Lee et al. |
| 2004/0006338 A1 | 1/2004 | Vetter et al. |
| 2004/0006355 A1 | 1/2004 | Vetter et al. |
| 2004/0077971 A1 | 4/2004 | Vetter et al. |
| 2004/0087872 A1 | 5/2004 | Anderson et al. |
| 2004/0176789 A1 | 9/2004 | Lee et al. |
| 2004/0255739 A1 | 12/2004 | Clifford et al. |
| 2005/0027291 A1 | 2/2005 | Lee et al. |
| 2005/0119652 A1 | 6/2005 | Vetter et al. |
| 2005/0124986 A1 | 6/2005 | Brounstein et al. |
| 2005/0182339 A1 | 8/2005 | Lee et al. |
| 2005/0222521 A1 | 10/2005 | Vetter et al. |

OTHER PUBLICATIONS

D'Angelo, Philip C., et al., "Stereotactic Excisional Breast Biopsies Utilizing the Advanced Breast Biopsy Instrumentation System." Am J Surg. 174: 297-302 (1997).

Ferzli, George S., et al., "Advanced Breast Biopsy Instrumentation: A Critique." J Am Coll Surg. 185: 145-151 (1997).

Rosen, Paul Peter, Rosen's Breast Pathology. Philadelphia: Lippincott-Raven Publishers, pp. 837-858 (1997).

Parker, Steve H., "Needle Selection." Percutaneous Breast Biopsy Eds. Parker, et al., Raven Press, New York, pp. 7-14 (1993).

Parker, Steve H., "Stereotactic Large-Core Breast Biopsy." Percutaneous Breast Biopsy Eds. Parker, et al., Raven Press, New York, pp. 61-79 (1993).

* cited by examiner

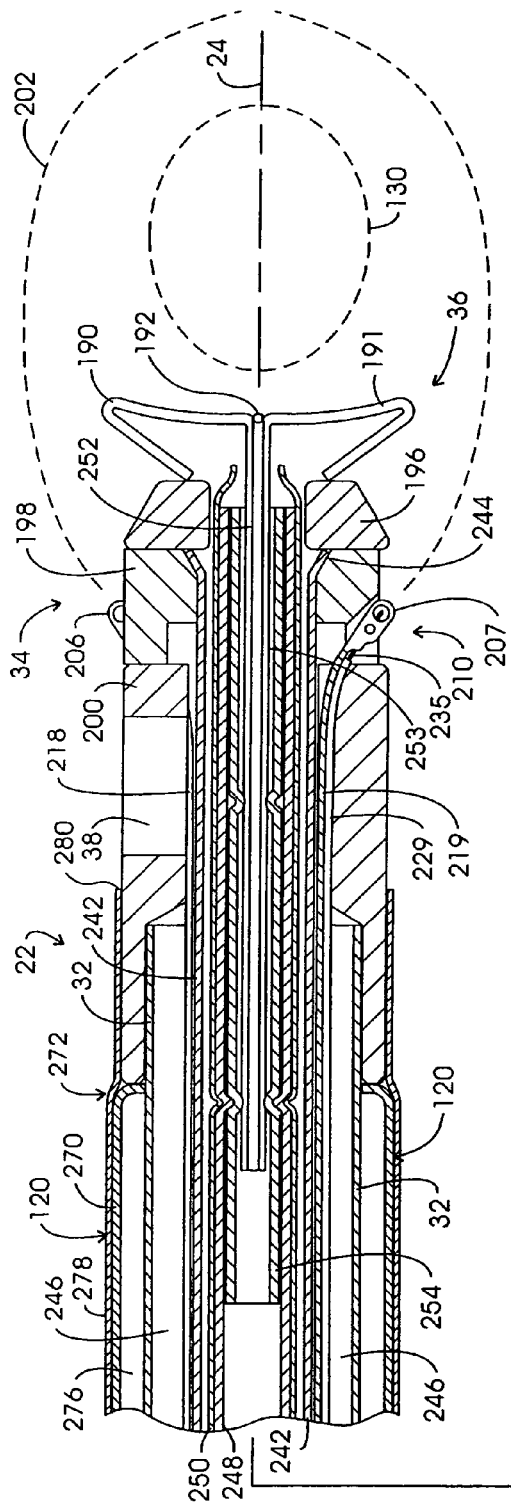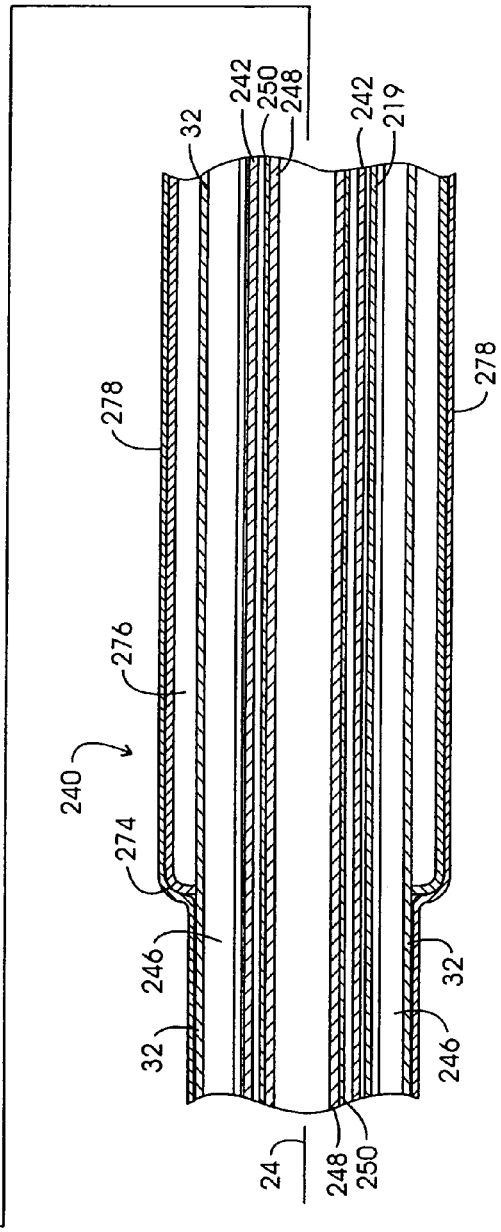
FIG. 5

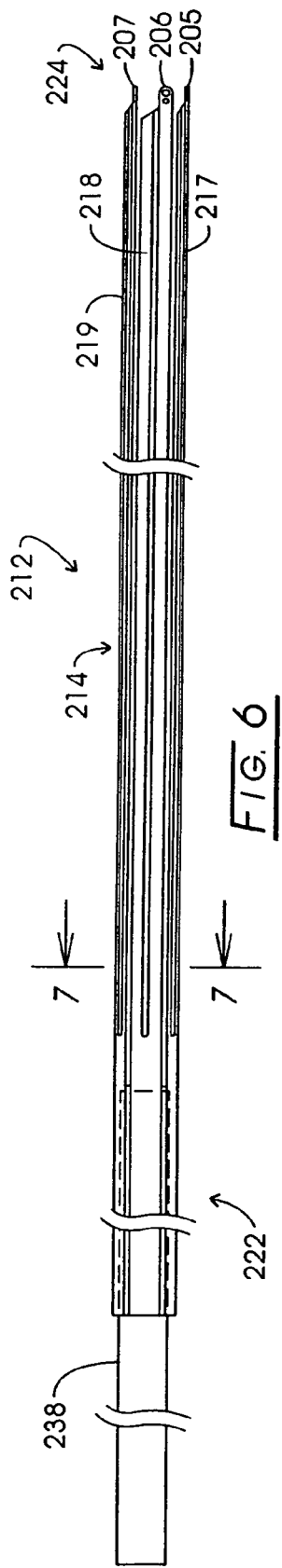
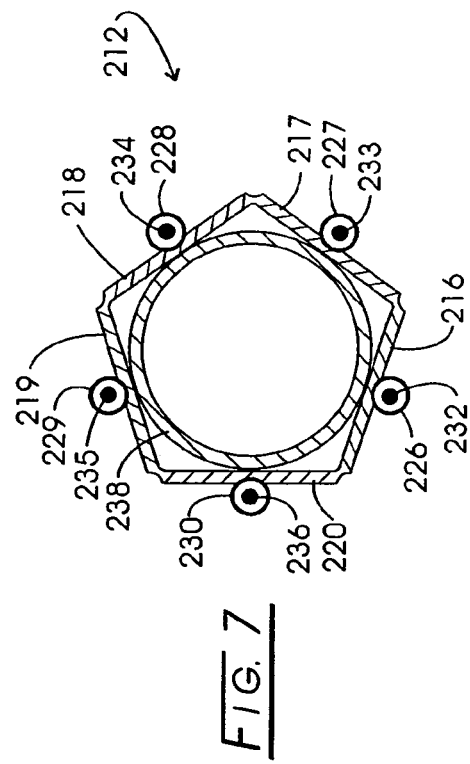
FIG. 6
FIG. 7

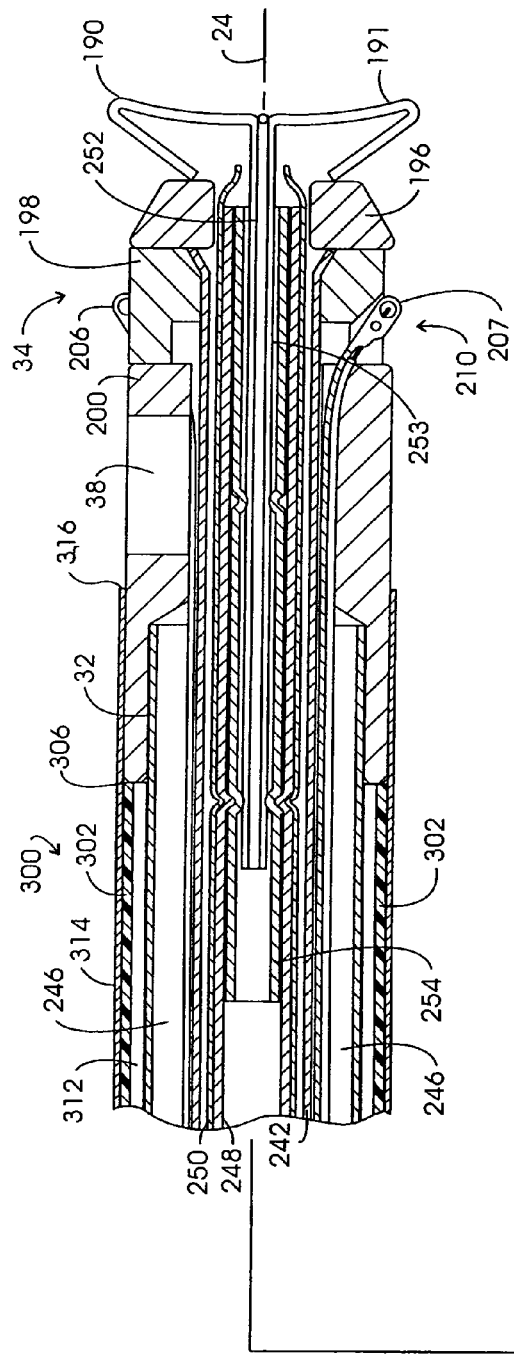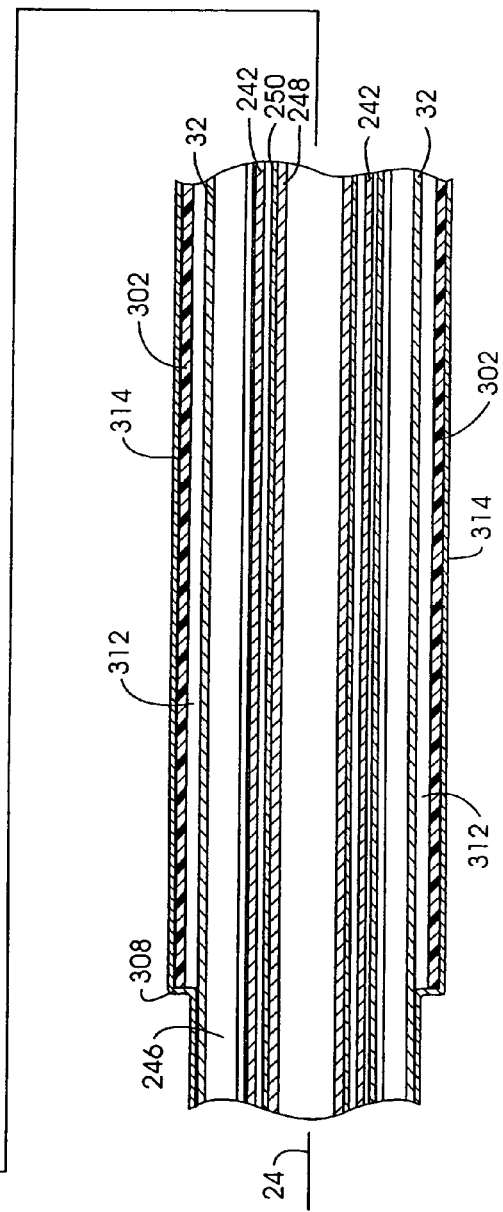
FIG. 15

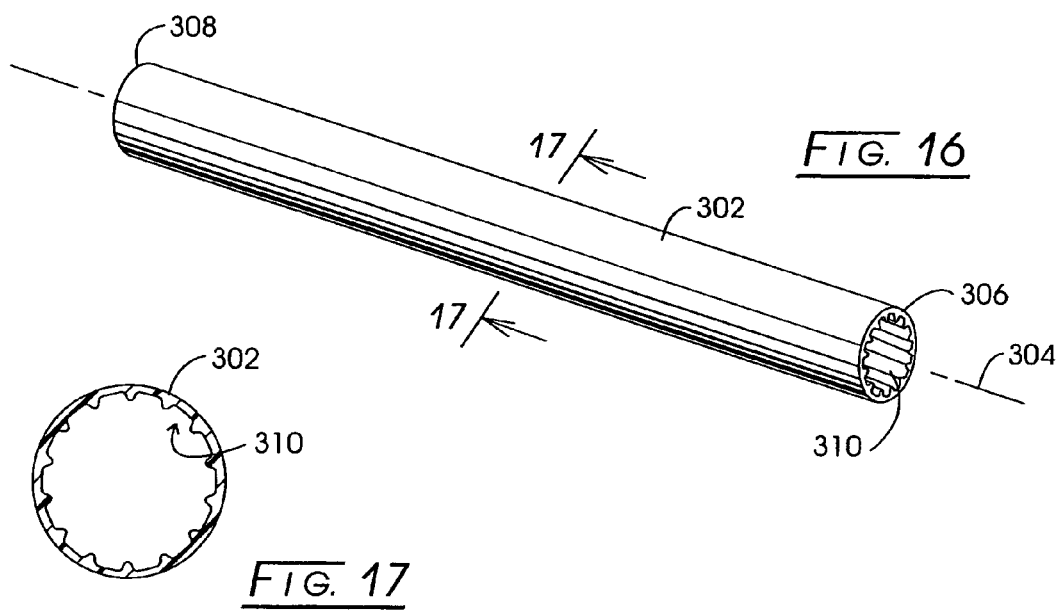
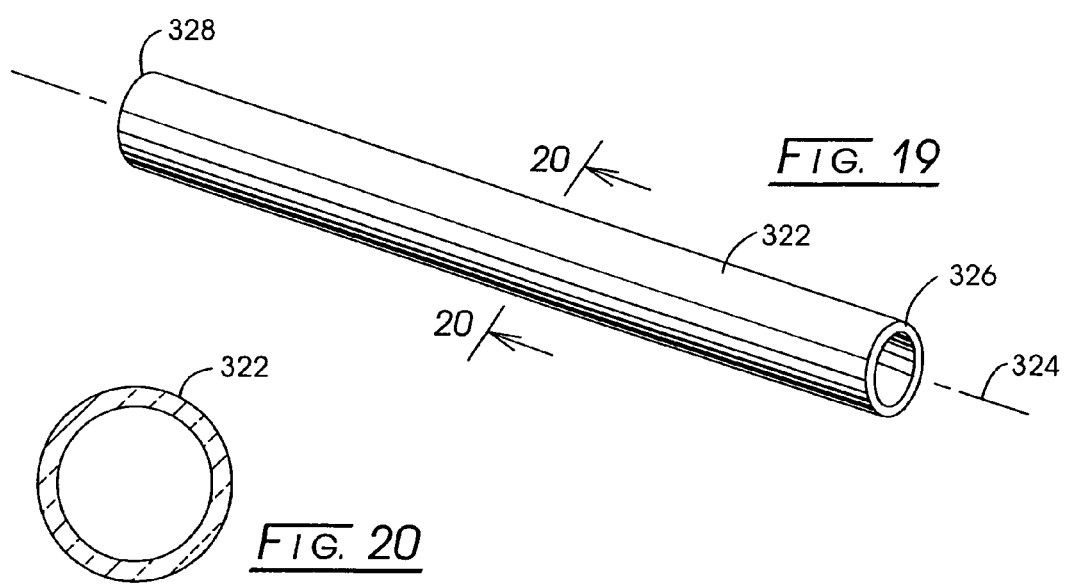

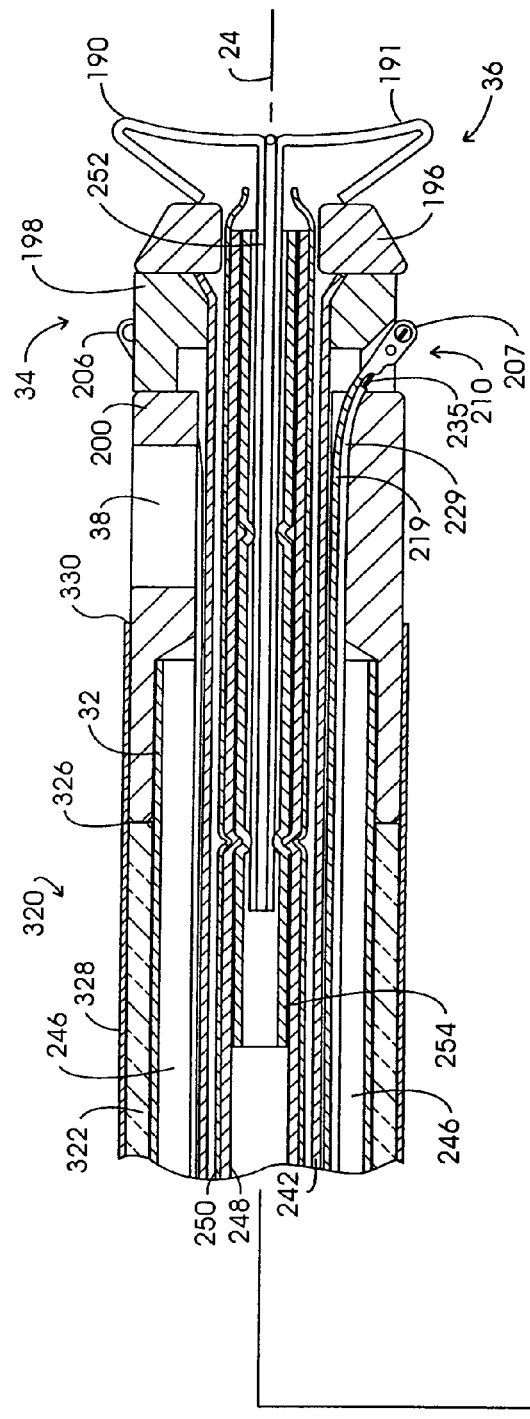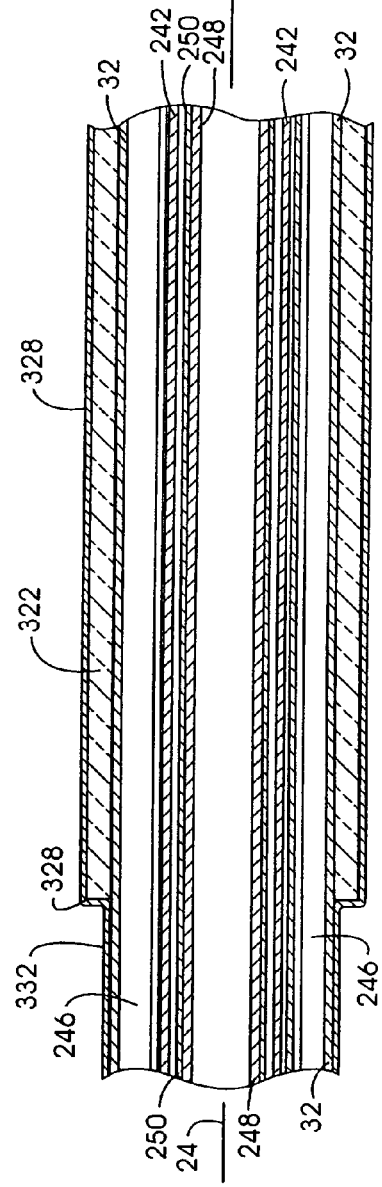
FIG. 18

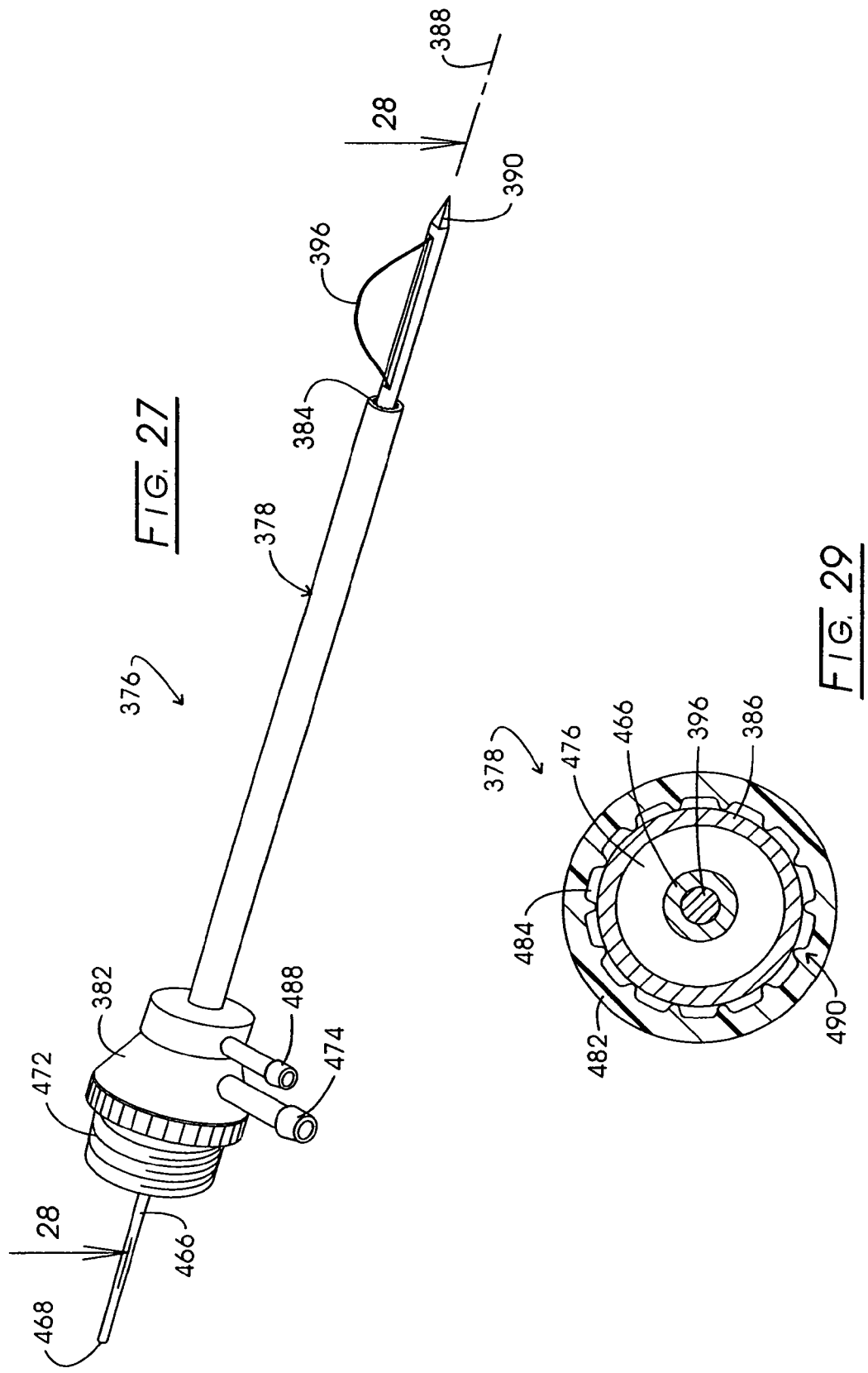

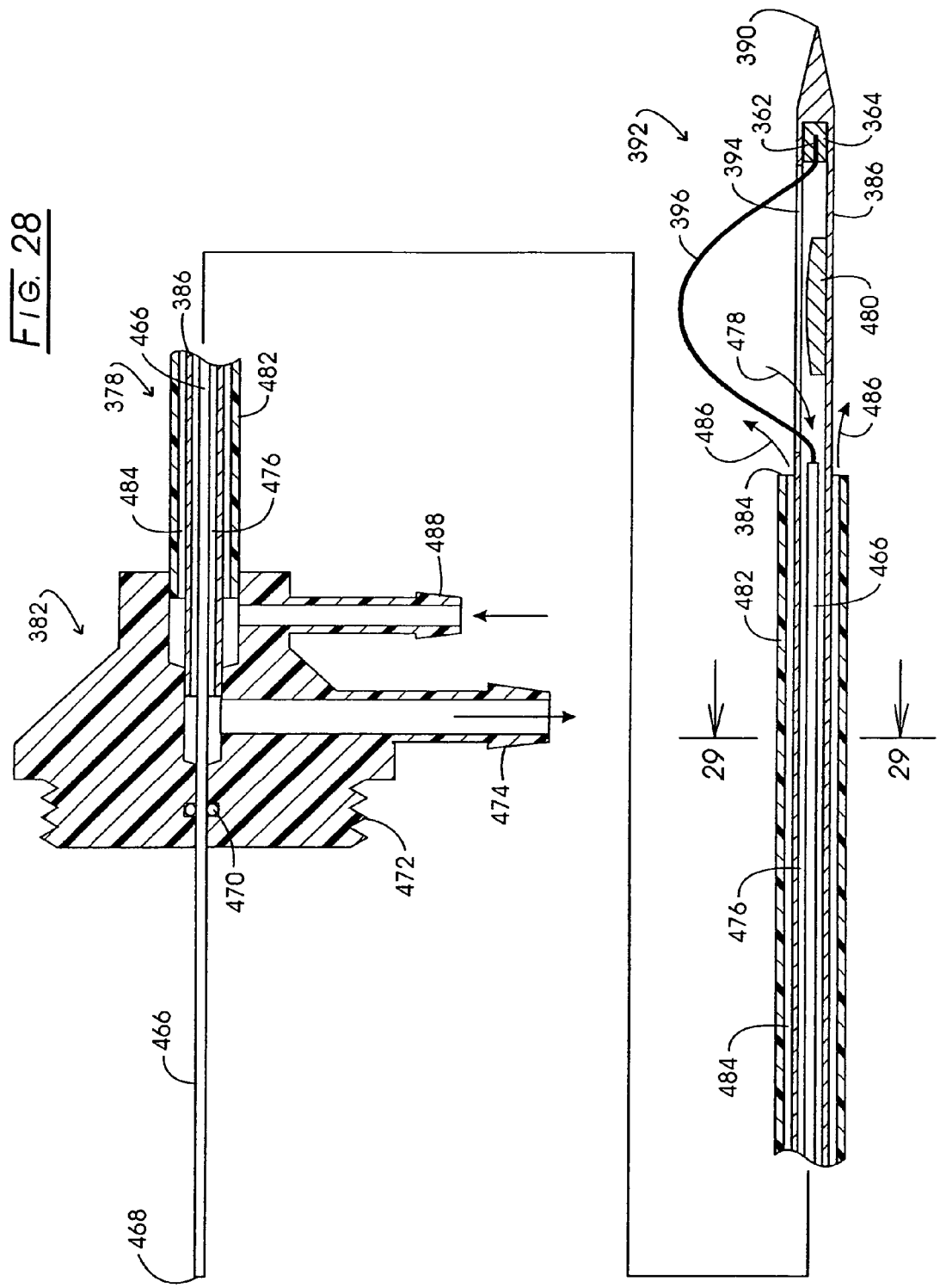

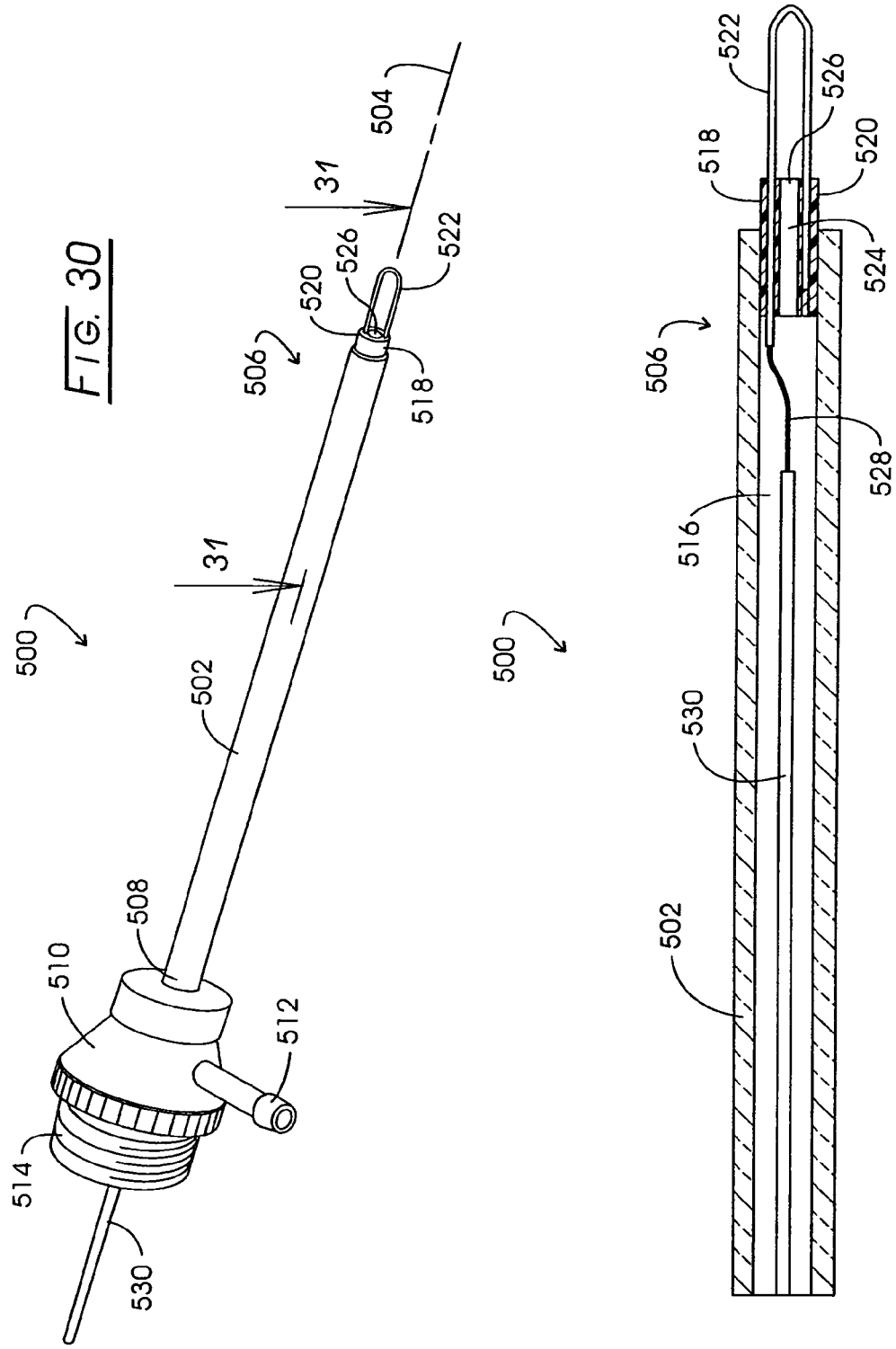

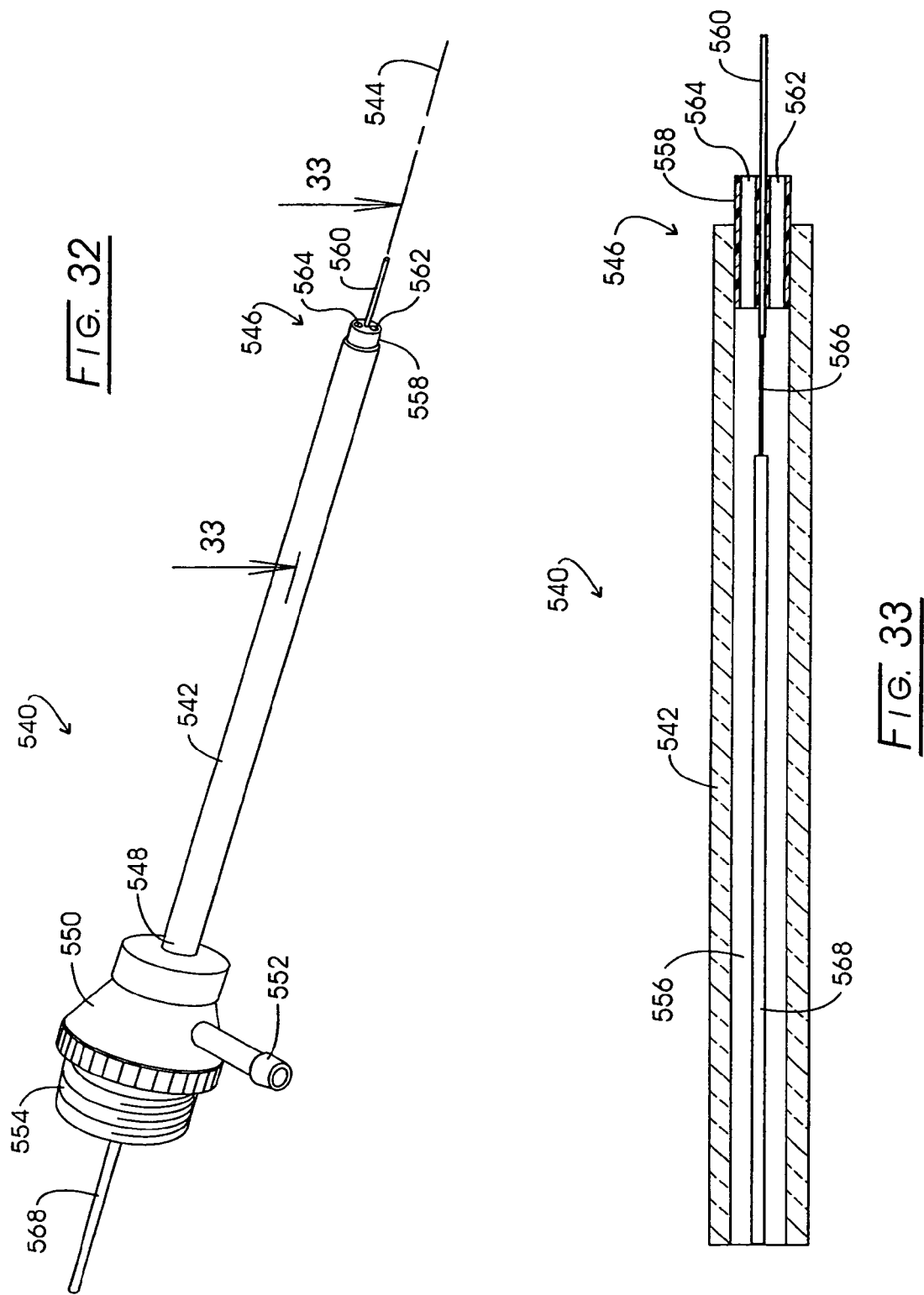

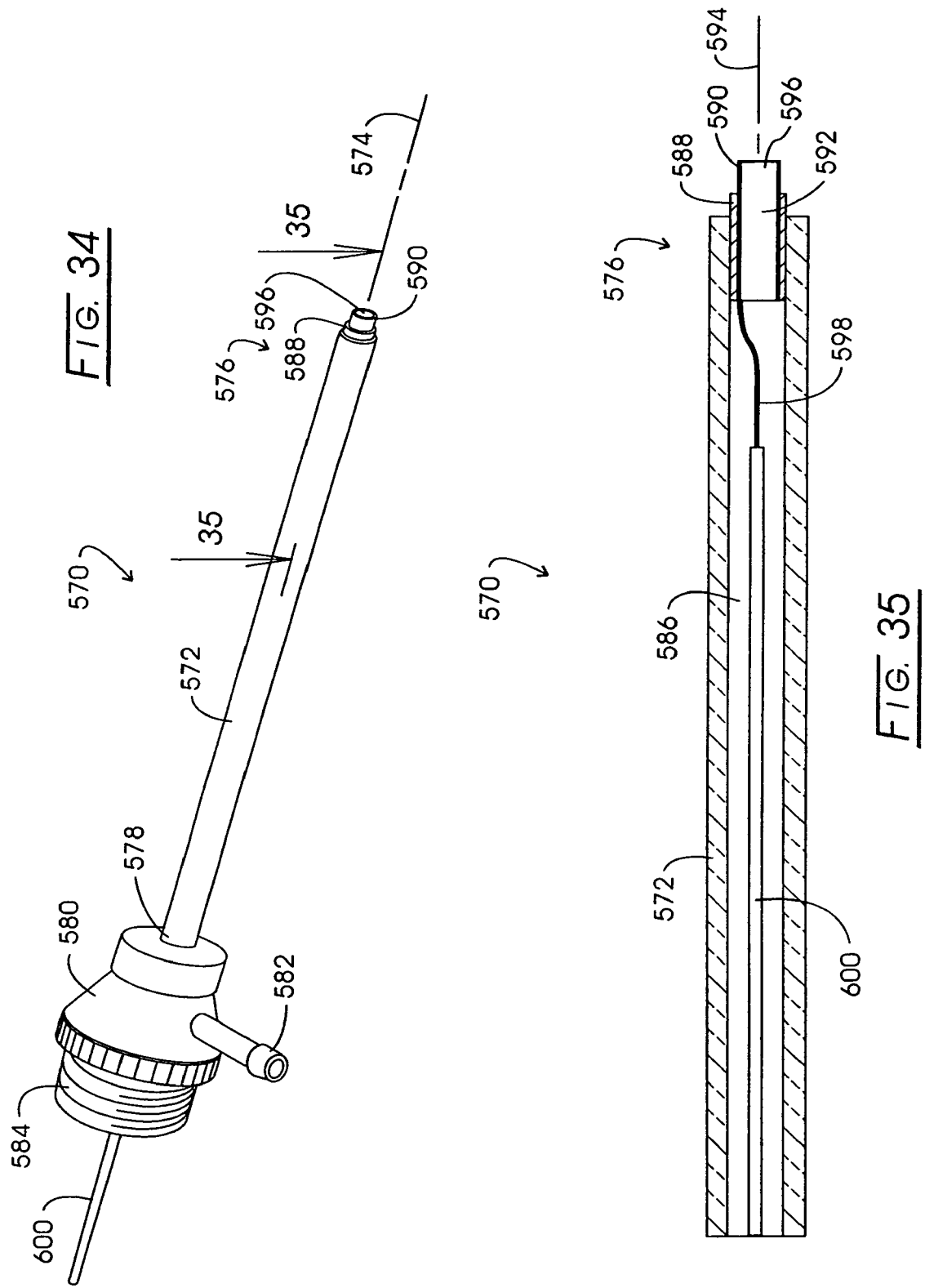

ELECTROSURGICAL ACCESSING OF TISSUE WITH CONTROLLED COLLATERAL THERMAL PHENOMENA

CROSS-REFERENCE TO RELATED APPLICATIONS

The present application is a division of application Ser. No. 10/630,100, filed Jul. 30, 2003 now U.S. Pat. No. 7,041,101 entitled "Electrosurgical Accessing of Tissue with Controlled Collateral Thermal Phenomena", which is a continuation-in-part of application Ser. No. 10/235,131, filed Sep. 5, 2002 (now abandoned) entitled "Method and Apparatus for Positioning a Tissue Recovery Instrument in Confronting Adjacency With a Target Tissue Volume" by Eggers, et al., which, in turn, is a continuation-in-part of application Serial No. 09/904,396 filed Jul. 12, 2001 now U. S. Pat. No. 6,471,659, entitled "Minimally Invasive Intact Recovery of Tissue", by Eggers, et al., which, in turn, is a continuation-in-part of application of Ser. No. 09/472,673, filed Dec. 27, 1999, now U.S. Pat. No. 6,277,083 by Eggers, et al., issued Aug. 21, 2001 and entitled "Minimally Invasive Intact Recovery of Tissue".

STATEMENT REGARDING FEDERALLY SPONSORED RESEARCH

Not applicable.

BACKGROUND OF THE INVENTION

The employment of high frequency current for the purpose of carrying out surgical cutting and/or coagulation has represented a significant surgical modality since its promotion in the 1920's by Cushing and Bovie. Electrosurgical cutting is achieved by disrupting or ablating tissue in immediate apposition to an excited cutting electrode, i.e., slightly spaced before it so as to permit the formation of a cutting arc. Continuous sine waveforms generally are employed to carry out the cutting function wherein tissue cells encountered by the electrode arc are vaporized. An advantage of this electrosurgical cutting procedure over the use of a cold scalpel, at least below the skin layer, resides both in an ease of cutting and a confinement of tissue damage, in the absence of collateral thermal phenomena, to very small and shallow regions. In this regard, cells adjacent the cutting electrode arc are vaporized and cells only a few layers deeper essentially are undamaged.

Inasmuch as these electrosurgical cutting and coagulation systems, for the most part, have been utilized in conjunction with what may be deemed "open" surgical procedures, the noted collateral thermal damage essentially has been dismissible. For instance, elevated temperature fluid including gases, liquid and steam generated by tissue cell vaporization immediately is disseminated to atmosphere, or in the case of abdominal laparoscopy, to an artificially developed inert atmospheric volume.

These cutting systems typically are employed in a monopolar manner wherein the cutting electrode is considered the active one and surgical current is returned from a large, dual component dispersive electrode coupled with the skin of the patient at a remote location. Other electrosurgical modalities typically are available with the generators employed with these systems. For example, various forms of coagulation employing discontinuous current waveforms may be carried out, including the use of a "blend" waveform devised for providing a combined cutting and coagulation electrode-carrying output. The generators also may perform in bipolar fashion, a return electrode being located at an instrument working end region.

The electrosurgical cutting reaction has been the subject of study. Some investigators have observed and thus contemplated a model wherein cutting is achieved as the electrical conduction of current heats the tissue up to boiling temperatures and, as noted above, the involved cells basically are exploded as a result of phase change. That phase change involves a generation of the noted elevated temperature fluid including steam with attendant latent heat of vaporization, a thermal attribute heretofore deemed to be of no physiological significance.

Another, parallel model has been described wherein, as an intense electromagnetic field impinges on absorbing tissue, an acoustic wave is generated by the thermal elastic properties of the tissue. The origin of the pressure wave lies in the inability of the tissue to maintain thermodynamic equilibrium when rapidly heated. As with the initial model described, a consequence of the reaction is the generation of elevated temperature fluid and attendant thermal phenomena. See generally:

(1) "Electrosurgery" by J. A. Pierce, John Wiley & Sons, New York, N.Y.

Electrosurgical systems have somewhat recently been introduced to what may be described as "embedded interstitial" surgical procedures. Important interest in such procedures has been manifested in achieving a minimally invasive access to potentially neoplastic lesions of the breast. These minimally invasive endeavors perhaps have been stimulated in consequence of estimates that one out of eight women will face a breast involved potentially cancerous lesion at some point in her life.

Access to these breast-involved lesions historically has been achieved through open surgery where the target tumor is removed along with a margin of healthy surrounding tissue. Over the somewhat recent past, non-electrosurgical preliminary minimally invasive biopsy procedures have been carried out to distinguished benign lesions from neoplastic ones. These preliminary approaches have involved: fine needle aspiration biopsy, vacuum assisted large core needle biopsies, Advanced Breast Biopsy Instrumentation (ABBI), and Minimally Invasive Breast Biopsy (MIBB). See generally:

(2) Parker, Steve H. "Needle Selection" and "Stereotactic Large-Core Breast Biopsy." *Percutaneous Breast Biopsy*. Eds. Parker, et al. New York: Raven Press, 1993. 7-14 and 61-79.

(3) Parker, Steve H. "The Advanced Breast Biopsy Instrumentation: Another Trojan Hourse?" Am. J. Radiology 1998; 171: 51-53.

(4) D'Angelo, Philip C., et al. "Stereotactic Excisional Breast Biopsies Utilizing the Advanced Breast Biopsy Instrumentation System." Am J Surg. 1997; 174: 297-302.

(5) Ferzli, George S., et al. "Advanced Breast Biopsy Instrumentation: A Critique." J Am Coll Surg 1997; 185: 145-151.

Relatively early as well as concurrent activities employing electrosurgical cutting implements in accessing breast born lesions generally involve an elongate probe, the distal or working end of which carries an electrosurgically excitable cutting edge. That cutting edge is sought to be excited when embedded in tissue, i.e., when positioned within or in adjacency with the lesion. Investigators have encountered serious difficulties in creating the necessary arc for carrying out a cutting maneuver. However, when such requisite arc formation is achieved, a variety of cutting electrode configurations have been and continue to be promulgated. For instance, the distal tip of the probe has been positioned in adjacency with the lesion, whereupon a wire-form cutting electrode is deployed while excited from a retracted orientation into a curvilinear shape which then is manipulated about the lesion in a circumscriptive maneuver, whereupon the electrode is retracted back into the probe structure. Where the thus vascularly isolated and compromised lesion is to be left in place, a barrier fluid may be introduced from the probe to enhance its isolation from adjacent healthy tissue. See, for example, U.S. Pat. No. 6,514,248 by Eggers, et al, entitled "Accurate Cutting About and Into Tissue Volumes With Electrosurgically Deployed Electrodes" issued Feb. 4, 2003.

A minimally invasive approach to accessing breast lesions wherein the lesion is removed in its entirety for diagnostic as well as therapeutic purposes has been described in U.S. Pat. No. 6,277,083 by Eggers, et al., entitled "Minimally Invasive Intact Recovery of Tissue", issued Aug. 21, 2001. This electrosurgically based instrumentation is of a variety wherein the active cutting electrodes, inter alia, move in a highly elaborate locus configuration with a geometry which alters active surface areas in the course of a circumscription procedure which initially isolates the target lesion and then captures it for submittal to analysis by pathology. The instrument employs an expandable metal capture component supporting forwardly disposed, arc sustaining electrosurgical cutting cables. Those cutting cables, upon passing over a target lesion, carry out a pursing activity to close about the target tissue establishing a configuration sometimes referred to as a "basket". To initially position the forward tip of the involved instrument in confronting adjacency apposite the targeted tissue volume, an assembly referred to as a "precursor electrode" assembly is employed. In the latter regard, the forwardmost portion of the instrument tip supports the precursor electrode assembly. That electrode assembly is initially positioned within a small incision at the commencement of the procedure, whereupon it is electrosurgically excited and the instrument tip then is advanced to a target confronting position. The utilization of such precursor electrodes as opposed to a sharpened tip cold trocar-like arrangement serves to avoid displacement of the target lesion by the instrument itself as it is maneuvered into confronting position.

An improved design for the instrument, now marketed under the trade designation EN-BLOC® by Neothermia Corporation of Natick Massachusetts is described in U.S. Pat. No. 6,471,659 by Eggers, et al., entitled "Minimally Invasive Intact Recovery of Tissue", issued Oct. 29, 2002. That patent also describes an electrosurgical generator which is, inter alia, configured to provide accommodation for the necessity of initially creating or "striking" an arc while the involved electrode is embedded within tissue. This initial creation of an arc is called for both at the commencement of probe or instrument positioning by creating an arc at the precursor electrode assembly and with respect to the capture component cutting and pursing cables both at the onset of the procedure and, for example, during an intermittent operation of the system as the capture component envelopes the targeted lesion. Because these electrodes are embedded or in direct contact with tissue, conventional surgical techniques for spacing the cutting electrode from the tissue to start an arc do not represent a practical approach to arc formation. To create such an arc at procedure commencement or for purposes of restarting during intermittent operation, the attending electrosurgical generator elevates a control voltage to an extent effecting arc creation at an elevated power level for a boost interval of time which is of that minimum duration necessary to assure development of an arc. Such a generator is marketed as a "Model 3000 Controller" by Neothermia Corporation (supra).

The "EN-BLOC®" instrumentation as discussed above further is characterized in the utilization of an evacuation system extending from a vacuum device to the instrument and thence through the elongate cannula or probe component thereof to four ingress ports located adjacent its tip or distal end. This evacuation system is activated during the utilization of the device for the purpose of collecting and removing liquids, for instance, which may be of such low resistance as to defeat arc formation, as well as smoke and steam.

Experience and a modeling form of analysis of the systems incorporating imbedded electrosurgical electrodes have revealed that the necessary confinement of the active electrodes within tissue during their excitation may lead to a substantial evocation of higher temperature thermal phenomena. The mechanism of electrosurgical cutting, involving arc generated steam vapor and other elevated temperature fluids for the duration required for target tissue volume circumscription may lead to collateral thermal damage to adjacent healthy tissue. Latent heat of vaporization of arc/cell generated fluids such as steam also may be conveyed through the surface of the elongate probe instrument itself into healthy tissue adjacent the path of insertion and removal.

Because the active cutting electrodes and associated elongate support components are located subcutaneously during a procedure, the anatomically and physiologically specialized boundary lamina protection barrier to external thermal attack represented by the skin is compromised by an interior heat attack. That same skin developed barrier to external phenomena may also be subject to the thermal (burn) damage occasion by a contact of proximal portions of the probe cannula with skin to induce burn or erythema. Skin contact with the steam/fluid heated probe cannula has been observed to be a particular possibility where guidance of the working end of the probe is assisted by ultrasound-based systems.

BRIEF SUMMARY OF THE INVENTION

The present invention is addressed to method, system and apparatus for carrying out interstitially located electrosurgical cutting while avoiding collateral thermal trauma to healthy tissue, as well as thermal damage to any target tissue specimen sought to be retrieved for biopsy.

As tissue is severed by application of an interstitially positioned electrosurgical cutting arc, elevated temperature fluids including steam, any heated gases and liquids including blood and anesthetic solution, are contemporaneously removed through an intake port located in the vicinity of tissue severance. These hot fluids are directed along a transfer channel for external disposition. As the elevated temperature fluids traverse the cannula component of an involved electrosurgical instrument, external surfaces of that instrument itself may be heated to tissue damaging temperatures. Such damage is avoided under the precepts of the instant invention by a variety of thermal insulation approaches, the selection of which may be predicated upon the ultimately developed physical size extent of the cutting electrode utilized and an attendant duration of the cutting procedure. In one instrument arrangement, a cannula component internally incorporating a heated fluid transfer channel is externally insulated by a thermal barrier configured as a thermal insulator sheath. That sheath may be provided as a tube having an inner wall surface spaced from the exterior surface of the cannula component. With such spacing, there is defined an insulation gap or space. Standoffs are employed to support the tube away from the cannula component surface, one such standoff being fashioned by rolling the ends of a stainless steel sheath tube.

In another embodiment the insulator sheath is formed as an extruded polymeric tube having an array of internally depending rib-form standoffs aligned in parallel with the axis of the cannular instrument.

As another feature, the invention provides a method for carrying out an electrosurgical cutting procedure at the subcutaneous situs of a target tissue volume situate within healthy tissue, comprising the steps of:

(a) providing an electrosurgical probe having a cannula component with a wall having an outward surface and extending along a probe axis from a supportable proximal end to a working end region having an electrosurgically energizable cutting assembly;

(b) providing an evacuation system having an intake port located at the working end region of the probe cannula component and having a transfer channel extending along the cannula component to an evacuation outlet;

(c) interstitially positioning the electrosurgical probe working end region in an operative orientation with respect to the target tissue volume effective to carry out the procedure;

(d) energizing the cutting assembly to effect formation of a cutting arc;

(e) carrying out the procedure by maneuvering the energized cutting assembly, the arc evoking elevated temperature fluid; and (f) removing at least a portion of the elevated temperature fluid through the evacuation system intake port and the transfer channel to an extent effective to avoid substantial thermal damage to the healthy tissue.

Other objects of the invention will, in part, be obvious and will, in part, appear hereinafter. The invention, accordingly, comprises the method, system and apparatus possessing the construction, combination of elements, arrangement of parts and steps which are exemplified in the following detailed description.

For a fuller understanding of the nature and objects of the invention, reference should be made to the following detailed description taken in connection with the accompanying drawings.

BRIEF DESCRIPTION OF THE DRAWINGS

FIG. 5 is a partial sectional view taken along the plane 5-5 shown in FIG. 4;

FIG. 6 is a side view showing a capture component employed with the instruments of the invention illustrating its structure at a stage of production;

FIG. 7 is a sectional view of a completed capture component;

FIG. 15 is a partial sectional view of an instrument according to the invention similar to FIG. 5 but depicting an alternate thermal shield structure;

FIG. 16 is a perspective view of another thermal shield embodiment according to the invention;

FIG. 17 is a sectional view taken through the plane 17-17 shown in FIG. 16;

FIG. 18 is a partial sectional view similar to FIG. 5 but showing another embodiment of a thermal shield according to the invention;

FIG. 19 is a perspective view of the thermal shield employed in connection with FIG. 18;

FIG. 20 is a sectional view taken through the plane 20-20 shown in FIG. 19;

FIG. 27 is an enlarged perspective view of a disposable component of an instrument employed with the system of FIG. 26;

FIG. 28 is a partial sectional view of the disposable component of the instrument illustrated in FIG. 26;

FIG. 29 is a sectional view taken through the plane 29-29 shown in FIG. 28;

FIG. 30 is a perspective view of another embodiment of a disposable probe component according to the invention;

FIG. 31 is a partial sectional view taken through the plane 31-31 shown in FIG. 30;

FIG. 32 is a perspective view of another embodiment of a disposable probe component incorporating the features of the invention;

FIG. 33 is a partial sectional view taken through the plane 33-33 shown in FIG. 32;

FIG. 34 is a perspective view of another embodiment of a disposable probe component according to the invention; and FIG. 35 is a partial sectional view taken through the plane 35-35 shown in FIG. 34.

DETAILED DESCRIPTION OF THE INVENTION

In the discourse to follow the thermal consequences of utilizing an electrosurgical cutting arc in an embedded, interstitial tissue environment are addressed. These consequence are, in effect, collateral to the generation of a cutting arc within a confined tissue environment. Accordingly, the system and method at hand looks both to the need for evacuating steam generated by boiling cell fluids heated gas or liquids (collectively "elevated temperature fluid") in order to avoid or at least minimize thermally induced trauma to surrounding healthy tissue, and looks to the consequences of instrument-born heat resulting from this process of evacuating generated steam and other fluids. Thermal data is provided which has been compiled from investigations carried out with the noted tissue retrieval system marketed under the trade designation "EN-BLOC®". Accordingly, that system is described along with modifications to it. The discourse then turns to applications concerning diverse electrosurgical cutting instruments having working end or forward regions which are utilized at interstitially embedded sites.

Figure 1:
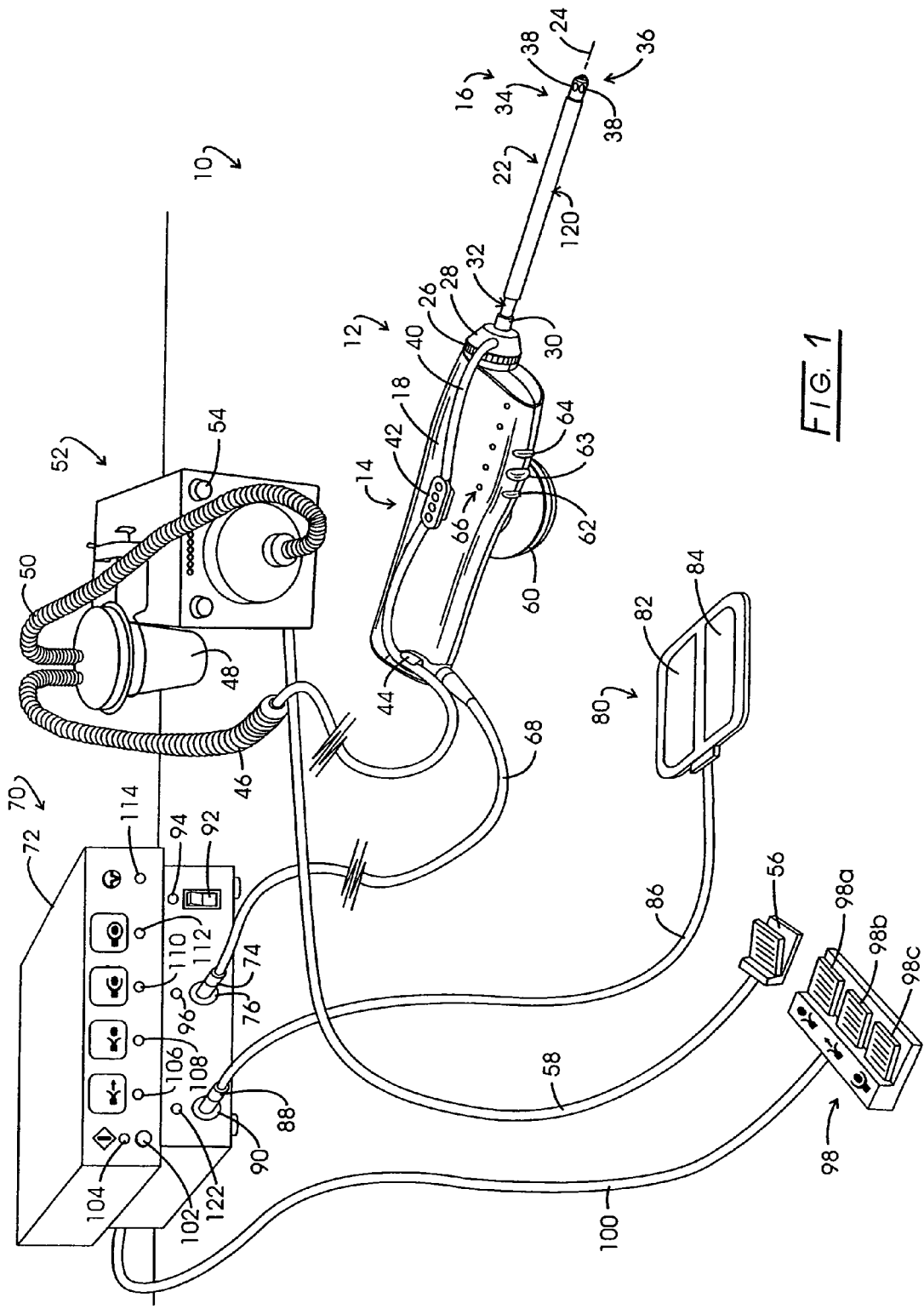
FIG. 1 is a perspective view of an electrosurgical system according to the invention.

Referring to FIG. 1, the noted system for isolating and retrieving a target tissue volume is illustrated in general at 10. System 10 comprises a tissue retrieval instrument represented generally at 12 which includes a reusable component represented generally at 14, sometimes referred to as a "handle". Instrument 12 additionally includes a disposable component represented generally at 16, the rearward portion of which is removably mounted within the polymeric housing 18 of reusable component 14.

Disposable component 16 includes an elongate cannula assembly represented generally at 22 which extends along a longitudinal cannula or instrument axis 24. The proximal end of cannula assembly 22 extends through a rotatable, externally threaded connector 26. Connector 26 is threadably engaged within the housing 18. Cannula assembly 22 further extends through a suction manifold 28 which is a component of an evacuation system. Manifold 28 is retained in position on cannula assembly 22 by a ferrule or collar 30 which is mounted over the outward surface of a cannula component, a portion of which is represented generally at 32. Most of the outward surface of the cannula assembly 22 will be seen to be covered with an electrically insulative thin black colored polyolefin shrink wrap or tube. The forward region or working end region of the cannula assembly 22, as represented generally at 34 extends to a distal end or tip represented generally at 36. Suction or vacuum manifold 28 is in vacuum conveying and fluid (steam/gas or smoke/liquid), receiving relationship through cannula assembly 22 with four intake ports, two of which are shown at 38 located at the forward region 34. Vacuum is conveyed to and fluid/steam/gas is received from suction manifold 28 via a flexible transparent polymeric tube 40. Tube 40 extends from an evacuation outlet (not shown) at manifold 28 into press fit connection with connectors 42 and 44, whereupon it is coupled with a flexible tube or hose of larger diametric extent shown at 46. Hose 46 extends to a fluid trap and filter assemblage 48 which is in vacuum communication via flexible hose 50 with the suction input of a suction pump assembly represented generally at 52. Vacuum or suction pump assembly 52 can be of a type marketed under the trade designation "VersaVac 2" by Stackhouse, Inc. of Palm Springs, Calif. Pump assembly 52 may be actuated into operation from a switch arrangement shown at 54 or through utilization of a footswitch 56 coupled to the pump assembly 52 via a cable 58.

Connectors as at 42 are positioned on each side of the housing 18 and function additionally to support a stabilizer handgrip, for example, the annulus-shaped grip represented at 60. Connectors as at 42 also may be employed to support the instrument 12 for stereotactic manipulation. Positioned at the forward portion of the housing 18 are three button switches 62-64 which function, respectively as an arm/disarm switch; an energize/position switch; and a start tissue capture switch. Immediately above the switches 62-64 on each side of housing 18 are linear arrays of light emitting diode (LED) based indicator or cueing lights, one such array being represented generally at 66. The visual cues provided by the indicators at 66, from the forward region of housing 18 toward the rear region thereof, provide a start/reset cue as a green light; a tissue capture complete cue provided as a green light; a start tissue capture cue (above switch 64) provided as a yellow light; an energize/position cue (above switch 63) provided as a yellow light; and an arm/disarm cue (above switch 62) provided as a green light. Energization and control is provided to the instrument 12 via a multi-strand cable 68 which connects with a combined control assembly and electrosurgical generator represented generally at 70 and incorporated within a console 72. Connection of the cable 68 with the console 72 is shown at a multi-lead connector 74 which is coupled to a console connector 76. The electrosurgically active electrode assembly of the instrument 12 performs in monopolar fashion. Thus, a conventional, relatively large, dispersive return electrode assembly, as shown in general at 80, is positioned against the skin surface of the patient. Assembly 80 is configured as having two electrode components 82 and 84 which are connected via cable 86 and connector 88 to console connector 90. Alternately, a return electrode may be positioned at the surface of cannula assembly 14 near its distal end in place of the illustrated use of a dispersive return 80.

Power is supplied to the circuitry at console 72 upon actuation of an on/off switch 92. When switch 92 is in an "on" orientation, a green visual indicator LED 94 located above the switch is energized. Proper connection of the cable 68 and connector 74 with console connector 76 is indicated by an illuminated green LED 96 positioned above connector 76. This connection test is carried out by directing current to a coding resistor within housing 18. A three-pedal footswitch represented generally at 98 is coupled via a cable 100 to the rear panel of console 72. The three pedals, 98a-98c of switch 98 emulate and provide alternative switching with respect to button switches 62-64.

Visual cueing corresponding with that at housing 18 LED arrays as at 66 also is provided at the console 72. In this regard, a start/reset switch 102 is operationally associated with an LED indicator 104 which illuminates in a green color upon actuation of that switch. An energize/position mode visual cue LED representing an energization of a precursor electrode at tip 36 is shown at 106. This LED provides a yellow output during the electrosurgical advancement of cannula assembly tip 36 into confronting adjacency with a targeted tissue volume. Next, a green, arm/capture mode visual cue is provided by an LED 108 to represent an arming of the tissue capture feature of instrument 12. Once an arm/disarm switch as at 62 or 98a is depressed, the energize/position switches as at 63 or 98b are no longer activatable. However, the practitioner may return to the positioning mode by again depressing an arm/disarm switch. A yellow capture mode visual cue is provided by an LED 110 to represent the start of and carrying out of a tissue capture procedure and upon completion of such capture, a green capture complete mode visual cue is provided by a green LED 112. A pause mode condition is represented by the energization of a green LED 114. In general, the pause mode is entered during a procedure by releasing capture switch 64 or footswitch 98c. When in a pause mode, the active capture electrodes of the instrument 12 are not energized and deployment of its capture component is halted. However, the evacuation function carried out by the suction pump assembly 52 continues to perform. To reenter the capture mode, the practitioner again depresses footswitch 98c or capture switch 64. Upon such re-actuation of the chosen switch, the capture mode continues, in effect, from the orientation where it left off. This pause mode of operation of the system may be employed by the practitioner during a capture mode of operation to permit, for example, the evacuation of fluids encountered by arc-based cutting components. Such fluids, may for example, be accumulations of local anesthetic solution, blood or the like.

An assurance that the vacuum system, at least to the extent that the vacuum pump assembly 52 is active, can be accomplished with a vacuum actuated switch (not shown) attached within the conduiting extending between the pump assembly 52 and the instrument 12. For example, unless such a switch is actuated, the commencement of a procedure can be logically blocked by the control assembly 70. In addition to the removal of smoke and such fluids as above discussed, the evacuation system including pump assembly 72, conduiting defining a transfer channel extending to the intake ports 38, functions to remove steam which is generated by the encounter of an electrosurgical cutting arc with the fluid of tissue cells. This removal of steam (as a component of elevated temperature fluid) serves, inter alia, to protect healthy tissue surrounding the region of cutting from thermal trauma. As such steam is evacuated, for example, along a transfer channel within cannula component 32 and into conduiting as at 40, it will tend to condense, releasing heat associated with the latent heat of vaporization of water. Accordingly, heat within the transfer channel of the cannula component 32 may, for certain orientations of the probe, cause an external surface burn to skin or erythema, notwithstanding potential damage to internally disposed healthy tissue. Accordingly, a thermal insulator sheath or shield assembly, shown generally at 120 is seen to be located over the cannula component 32. The performance of this shield and others is discussed later herein. Not seen in the instant figure is a very thin electrically insulative and biocompatible covering of the sheath assembly 120 and adjacent portions of the cannula component 22.

At the time the connector 88 of the return electrode 80 is coupled to console connector 90 and switch 92 is in a power-on condition, a patient circuit safety monitor (PCSM) carries out a self test. On subsequent actuation of the start/reset switch 102, a fault test with respect to the two electrode components 82 and 84 is performed. In the event the later test fails, then both visual and aural pulsating warning cues are activated, the visual cue being provided at a red LED 122 located adjacent connector 90.

Figure 2:
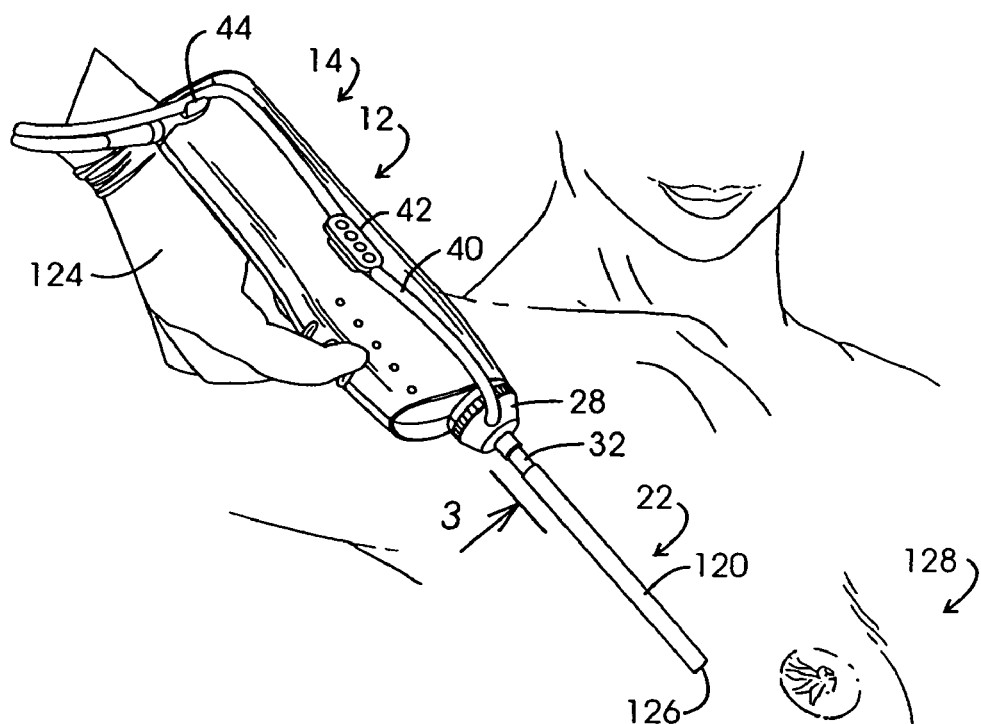
FIG. 2 is a perspective view illustrating one stage in a tissue retrieval/biopsy procedure employed with an instrument configured according to the invention.
Figure 3:
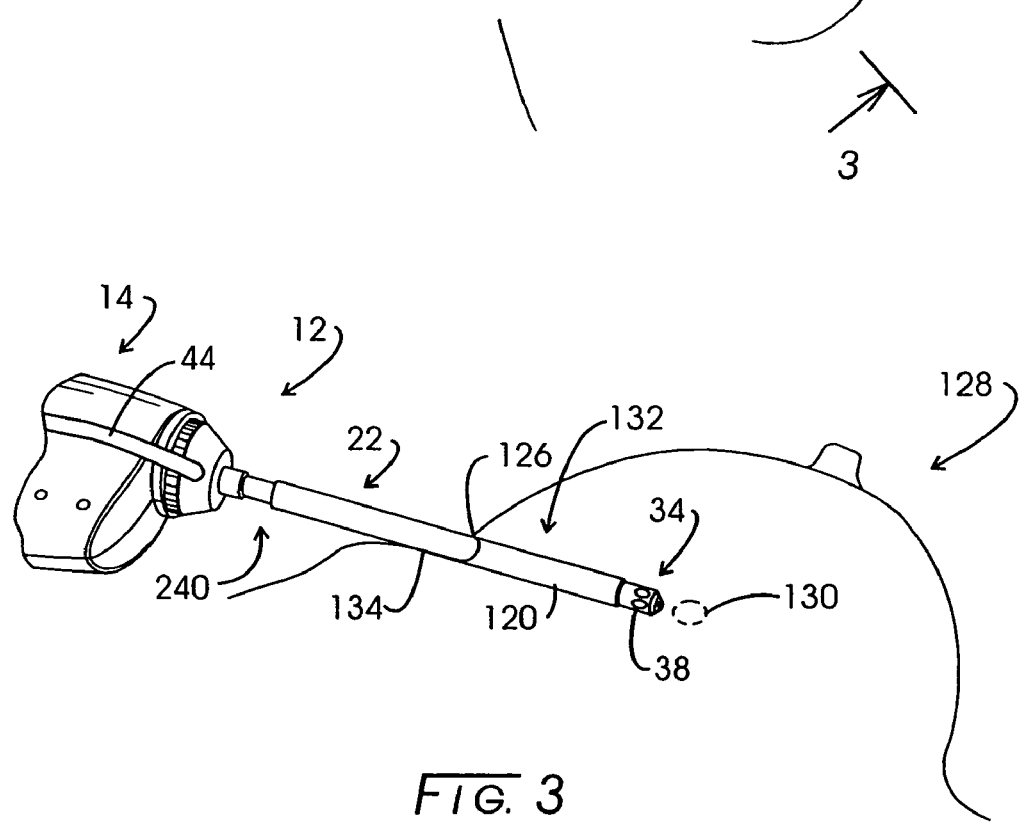
FIG. 3 is a perspective view taken along the site lines 3-3 shown in FIG. 2.

The protectional functioning of the thermal insulator sheath assembly 120 is demonstrated in connection with FIGS. 2 and 3. Looking to FIG. 2, the instrument 12 is seen to be supported by the hand 124 of a practitioner as the cannula assembly 22 extends within an incision 126 within breast region 128 of a patient. The instant demonstration is one which typically involves ultrasonic guidance. That guidance is employed, as represented in FIG. 3, to move the forward or working end region 34 of the cannula assembly 22 into confronting adjacency with a target tissue volume or lesion represented symbolically in phantom at 130. Note that the cannula assembly 22 is in contact with surrounding interstitially disposed tissue represented generally at 132, as well as in contact with external skin surface at region 134. Steam created by the electrosurgical cutting arc of precursor electrodes at the tip of the cannula assembly 22 and as a consequence of the deployment of a capture component will be evacuated by a transfer channel extending through cannula component 32 and thence into conduiting 44. Without protection as provided, for example, by the sheath assembly 120, thermally induced tissue trauma both externally and interiorally may be occasioned.

Figure 4:
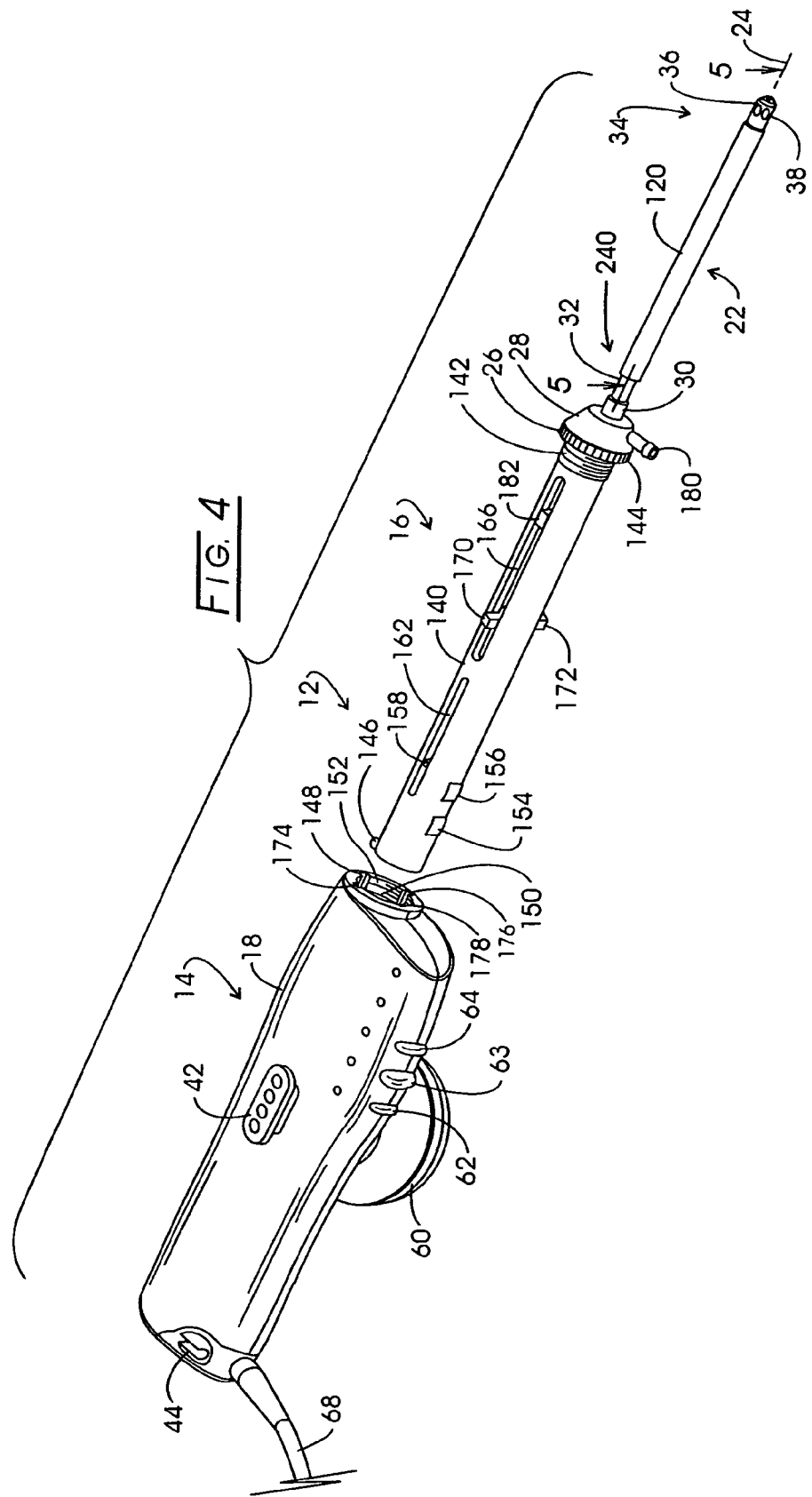
FIG. 4 is an exploded view of an electrosurgical instrument configured in accordance with the invention.

Referring to FIG. 4 the disposable component 16 of instrument 12 is revealed in an orientation prior to its insertion within the housing 18 of reusable component 14. This disposable component 14 is sometimes referred to as the "probe". In the figure, cannula assembly 22 is seen extending forwardly from a cylindrically-shaped support housing 140. The forward region of support housing 140 supports the rotatable connector 26. In this regard, it may be observed that the connector 26 is configured with external threads 142 which are fixed for rotation with a knurled flange 144. At the rearward end of support housing 140 there is located an upstanding indexing pin 146 which, during installation of the disposable component 16, is slidably received within an upwardly disposed elongate slot 148 extending internally along an elongate receiving cavity 150. Internal threads 152 within cavity 150 threadably engage the external threads 142 of connector 26 when the disposable component 16 is inserted within the reusuable component 14.

Positioned opposite indexing pin 146 on support housing 140 are two, spaced apart electrical contacts 154 and 156 which are oriented to make wiping contact with corresponding electrical terminals disposed within housing 18 upon insertion of support housing 140 within the receiving cavity 150. Contacts 154 and 156 selectively receive electrosurgical cutting current which is applied respectively to a precursor electrode assembly at tip 36 and the electrosurgical cutting and pursing cables associated with a capture component retained within cannula assembly 22. Those pursing cables extend from the capture component within cannula component 32 to a cable terminator component having guidance tabs or ears, one of which is revealed at 158 slidably mounted within an elongate stabilizer slot 162 arranged in parallel with axis 24. A corresponding guidance tab and slot combination is found at the opposite side of support housing 140. Located forwardly of the slots as at 162 are two, additional elongate drive slots, one of which is shown at 166 similarly arranged in parallel with axis 24. The outwardly extending ears or guide tabs of a drive assembly drive member extend from these slots and are seen at 170 and 172. These ears or tabs 170 and 172 support rearwardly disposed driven surfaces which are used to impart forward movement to the drive assembly. This forward movement functions to deploy a capture component from cannula component 32. When the support housing 140 is installed within the receiving cavity 150 of housing 18, these tabs 170 and 172 pass through oppositely disposed notches shown respectively at 174 and 176 provided at a forward portion of housing 18. Similarly, a notch 178 is located forwardly within housing 18 to permit passage of the electrical terminals 154 and 156.

The procedure for installing the disposable component 16 within the reusable component 14 involves the sliding of disposable support housing 140 within the receiving cavity 150 and rotating knurled portion 144 of connector 26 to provide for the engagement of threads 142 with threads 152. Upon completing the assembly, the flexible transparent tube 40 of the evacuation assembly may be attached to an evacuation outlet 180 depending outwardly and in fluid and suction or vacuum communication with suction manifold 28. Finally, a tab at 182 is seen extending through a forward portion of the drive slot 166. This tab may be a component of a drive assembly safety stop functioning to limit the extent of forward travel permitted by a drive member component of the ears 170 and 172. It is located in accordance with a pre-selected capture component maximum effective diametric extent. Such a tab also may function as a capture complete stop which functions in the derivation of a capture complete signal conveyed to the control assembly 70. Further details of the system 10 including control assembly 70 are provided in the above-referenced U.S. Pat. No. 6,471,659 which is incorporated herein by reference.

Referring to FIG. 5, details of the working end or forward region 34 and tip 36 of the cannula assembly 22 are revealed. Tip 36 is depicted as it is utilized for capturing tissue volumes having a principal diametric extent of, for example, extending from about 10 mm to about 20 mm. The tip incorporates four precursor electrode components arranged in quadrature or cross-shaped symmetrically about longitudinal axis 24. Three of the elongate generally L-shaped precursor electrodes are revealed at 190-192. When electrosurgically excited, the forward surfaces of these stainless steel wire electrodes function to support a cutting arc. Those forward precursor electrode components are, in turn, located just forwardly of a truncated cone-shaped ceramic (alumina) protective tip 196. Tip 196 functions to provide an arc-resistant or arc isolating tip portion preventing its thermal breakdown. Component 200 is seen to provide the earlier-described four intake ports 38 and is supported from the cannula component 32. Component 198, in cooperation with component 200 provides a ramp structure for a sequence of five thin stainless steel leafs of a capture component, the tips of which carry braided multi-strand stainless steel pursing cables which are electrosurgically excited to create an arc for cutting purposes and which create a pursing action while cutting to form a basket or cage-like structure around a targeted tissue volume. In the latter regard, a schematic or stylized profile of the travel of these leafs and associated cabling is shown as a phantom locus 202 circumscribing a target tissue volume such as the target tissue volume 130 shown in FIG. 3 which numerical identification reappears in the instant figure. As an alternative arrangement, the precursor electrodes, capture component leafs, pursing cables as well as cannula wall and associated components may be constructed of non-ferromagnetic material (e.g., titanium, nitinol) to enable use of this device with magnetic resonance image guidance of a biopsy procedure. Drive imparted to these capture components leafs emanates from the mechanism associated with ears 170 and 172 described in connection with FIG. 4. Each of these leafs terminates in an eyelet structure at its leading edge, two such eyelet structures being identified at 206 and 207. The polymeric tip components 198 and 200 cooperate to form a guidance assembly represented generally at 210 which functions to direct the leafs of the capture component, appropriately spaced apart and at a proper attack angle in a capture maneuver. That attack angle for the instant embodiment is about 45°.

Cannula component 32 has a relatively small diametric extent, for example, about 5 mm. Within forward region 34 there is disposed an earlier-noted capture component comprised of a pentagonally-shaped stainless steel elongate leaf structure with a leaf leading edge formed with dual apertures or eyelets which carry a five pursing cable assembly.

Referring momentarily to FIG. 6, the capture component is represented generally at 212 at a stage in its fabrication prior to the attachment of the noted pursing cables as well as polymeric guide tubes. As revealed in the sectional view of FIG. 7, the capture component 212 has a generally pentagonal cross-sectional configuration initially chemically milled from flat stainless steel stock such that the forward portion 214 is formed with a sequence of five leafs having a thickness within a range of about a 0.0025 inch to about a 0.005 inch and preferably of 0.003 inch and a widthwise extent of 0.080 inch. The five leafs are shown in these figures at 216-220 and extend from a pentagonal base portion 222 (FIG. 6) to the noted dual aperture containing tips, the combination of which is represented in general at 224 in FIG. 6. Each of the leafs 216-220 is chemically milled with a somewhat centrally disposed groove extending longitudinally along its length. Within each groove, as seen in FIG. 7, there is adhered a polyimide flexible guide tube. These guide tubes are quite small, having, for example, an outside diameter of about 0.020 inch and a wall thickness of about 0.0015 inch. The guide tubes are shown in FIG. 7 at 226-230 as being adhesively attached to respective leafs 216-220. Each of the guide tubes 226-230 slidably guides a pursing cable as shown respectively at 232-236. These nineteen-strand stainless steel cables are formed, for example, of type 316 stainless steel and exhibit, when combined, a nominal diameter of about 0.006 inch. The corresponding strand diameters will be about 1.2 mils for that diameter. In general, the sizing of the cables is determined with respect to maintaining requisite strengths at electrosurgical excitation temperatures ranging from about 1400° F. to 1600° F. and these components further must retain a capability for readily "playing out" or passing through the eyelet structures during the initial phase of target tissue capture and evenly responding during their pursing activity at the later stages of capture. The polyimide guide tubes 226-230 are attached to the chemically etched grooves within the leafs by initially adhesively coupling them to those troughs. Then, the tubes are bonded to a corresponding leaf within the chemically milled groove utilizing an electrically insulating coating material and process which achieves bonding and provides requisite electrical insulation for the entire capture component assembly 212. That coating, which has a thickness of about 0.001 inch, is a vapor-phase polymerized conformal coating marketed under the trade designation "Parylene". Parylene is the generic name for members of a polymer series. The basic member of the series, called Parylene C is a poly-para-xylene, a completely linear, highly crystalline material. Such coatings are available from Parylene coating service companies such as Specialty Coating Systems, of Indianapolis, Ind.

FIG. 6 reveals the eyelet structure 224 at the leading edge of capture component 212. The leading edges containing eyelets are bent outwardly from the orientation shown prior to the attachment to and extension of cable through them. Further, the capture component 212 is weldably attached to a drive tube or drive member 238 which extends rearwardly into support housing 140 and into engagement with the drive member associated with the tabs or ears 170 and 172 (FIG. 2).

Returning to FIG. 5, the forward or working end region of the cannula component 22 is again represented at 34, while the proximal region of that component is revealed at 240. The structure of the cannula assembly 22 looking inboard from cannula component 32 is seen to include the capture component assembly 212, one leaf, 219 of that assembly being revealed in section and another being shown at 218. Note the now outwardly bent orientation of the eyelets for the leaf structures. Extending next inwardly inboard is a stainless steel support tube 242 which is mounted at the rear portion of the support housing 140 of disposable component 16 and extends forwardly through cannula component 32 to a flared region 244 engaging polymeric tip component 198. This flaring is found to be helpful in permitting the support tube to overcome the rather substantial forwardly directed forces occurring during forward deployment of the capture component leafs and cables. Note additionally, that the somewhat annular space between the wall of cannula component 32 and support tube 242 provides the noted evacuation system transfer channel diverting elevated temperature fluid including steam, shown generally at 246. Channel 246 extends from the intake ports 38 at forward region 34 to suction manifold 28 and its associated evacuation outlet 180 (FIG. 4).

Located inside support tube 242 is an electrosurgical precursor electrode tube 248 which also extends to the rearward portion of support housing 140 for purposes of both support and receiving electrosurgical cutting energy transmitted through electrical contact 154 (FIG. 4). As the precursor electrode tube 248 extends rearwardly, it is electrically insulated from support tube 242 by a polymeric shrink wrap 250.

The precursor electrodes are mounted as a subassembly of four stainless steel electrode wires having the noted generally elongate L-shape as seen, in particular, at 190 and 191 in the instant figure. Elongate components of the precursor electrodes, for example, as identified at 252 and 253 with respect to electrodes 190 and 191 extend into a subassembly tube 254. Four such electrode assemblies are crimped inside of this tube 254 and that tube, 254, in turn is crimped within the forward portion of the precursor electrode tube 248. It has been found that the utilization of four cutting surfaces for the precursor electrodes, arranged in the cross-shaped pattern, provides preferable instrument positioning results. The resultant arrangement of confronting electrode surfaces is revealed, for example, in connection with FIGS. 8 and 9. In general, precursor electrodes 190-193 will have a tissue cutting and confronting length of about 6.5 mm to about 7.0 mm for employment with a maximum effective capture diameter for the capture component 212 of 10 mm to 20 mm. Where that effective diameter expands above 20 mm up to 40 mm, the corresponding expanse of the precursor electrodes or their lengthwise confronting extent will be about 10 mm to about 15 mm. When configured having one of the larger lengthwise extents, the electrodes are slightly canted forwardly and are made resilient so as to be capable of flexing forwardly as the electrosurgically excited pursing cables physically contact the precursor electrodes. During this procedure, the precursor electrodes are open-circuited and permitted to be reenergized as they are urged into alignment with the capture component leafs. This temporary re-energization of the longer precursor electrodes is found to be beneficial as the electrodes retract or bend toward the larger tissue samples being captured.

Figure 8:
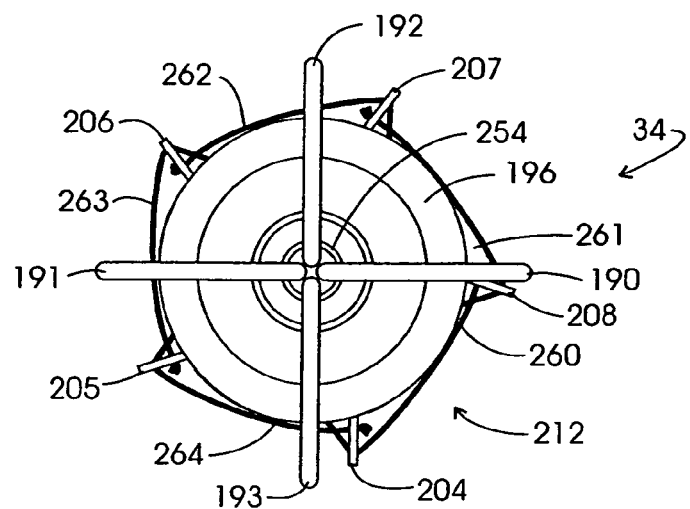
FIG. 8 is a front view of an instrument according to the invention showing a capture component in a retracted orientation.
Figure 9:
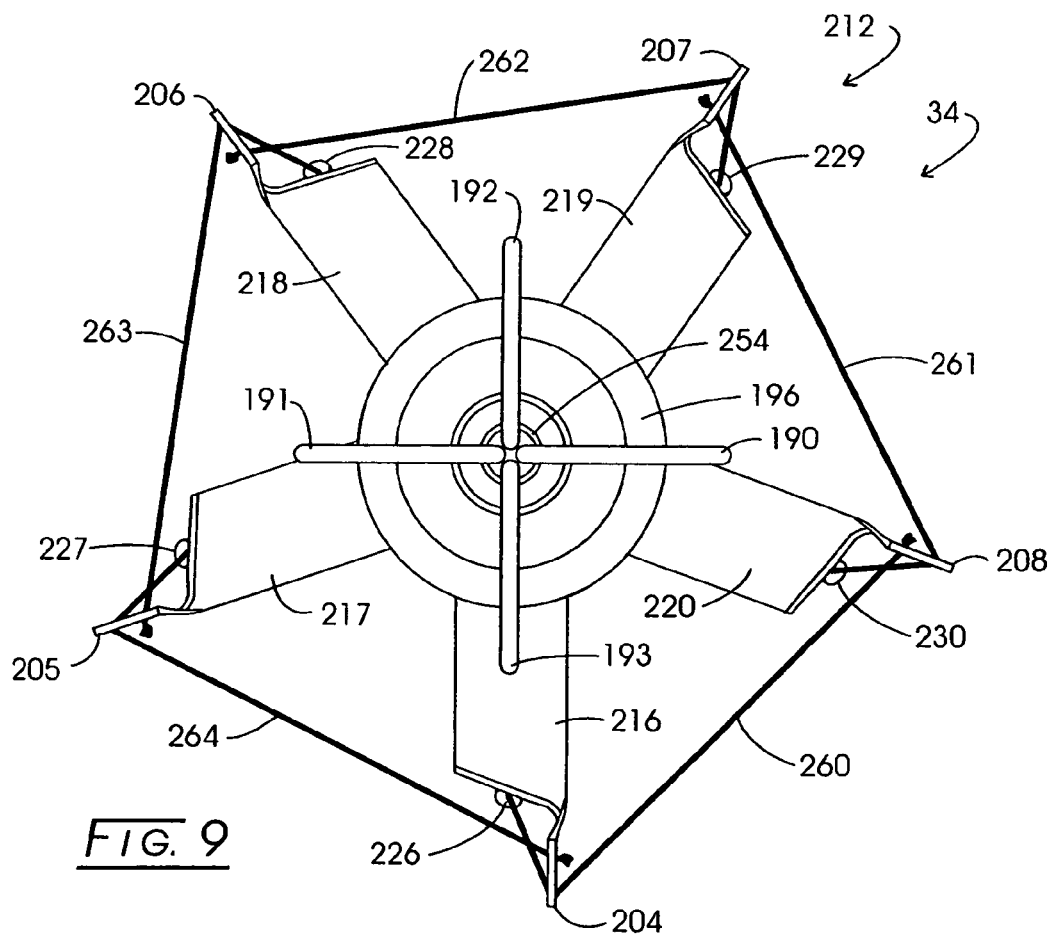
FIG. 9 is a front view of the instrument of FIG. 8 showing the capture component thereof at a stage in its deployment.

FIGS. 8 and 9 present front views of the cannula assembly 22 forward or working end region 34 illustrating in particular the orientation of the precursor electrodes as well as the leafs and cables. In this regard, those cables and leafs are in a retracted state in FIG. 8. In contrast, FIG. 9 reveals an orientation of the leafs and cables as they are being deployed toward their maximum diametric extent. FIG. 9 reveals that cable 260 emerges from guide tube 226 to pass through eyelet structure 204 and extends to knotted connection with eyelet structure 208 of leaf 220. Similarly, cable 261 extends from guide tube 230, passes through eyelet structure 208 and is tied off at eyelet 207. Cable 262 emerges from guide tube 229 at leaf 219, extends through eyelet structure 207 and is tied off at eyelet structure 206. Cable 263 emerges from guide tube 228, extends through eyelet structure 206 and is tied off at eyelet structure 205. Lastly, cable 264 emerges from guide tube 227 at leaf 217, passes through eyelet structure 205 and is tied off at eyelet structure 204.

In the procedure initiation orientation of FIG. 8, the active area extent exhibited by the electrosurgically cutting portions of cables 260-264 is somewhat small but slightly larger than at full pursing at the completion of the procedure. In the figure, the five eyelet structures 204-208 are visible in connection with portions of the pursing cables 260-264. When in this orientation, the precursor electrodes 190-193 will have been excited to form an arc while the instrument 12 is maneuvered into an orientation as represented in FIG. 3 wherein the tip 36 is in confronting targeted tissue volume, a geometry shown in stylized fashion in FIG. 5. Throughout this positioning procedure, positional elevated temperature fluid including steam will have been generated in the resultant locus of cutting travel of the precursor electrodes which will, in turn, have been evacuated by the evacuation system through ports 38 and along the transfer channel 246 (FIG. 5). The precursor electrode structure then is deactivated (open circuited) and the capture component 212 is deployed in conjunction with the arc-forming excitation of the confronting portions of pursing cables 260-264 with electrosurgical cutting energy. As in the initial excitation of the precursor electrodes, however, inasmuch as these confronting portions of the cables are embedded in tissue, a boost control voltage is called for a noted boost interval adequate to evoke formation of a cutting arc along the electrosurgically active portions of cables 260-264. In general, that boost interval occurs just before deployment of the capture component 212. FIG. 9 reveals that, as the leafs of capture component 212 are deployed, the pursing cables 260-264 are being "played out" and the effective diametric extent of the capture component is expanding to circumscribe the targeted tissue volume to be removed, or alternately, to remove a sample from a lesion. As before, the interval of cutting will vary in conjunction with the maximum diametric extent developed by the capture component. Thus, during this interval smoke, other fluids and, particularly, steam is being evacuated from the locus of the circumscriptive tissue isolating cut. Such fluids including steam are directed along the transfer channel 246 (FIG. 5) to suction manifold 28 and evacuation outlet 180 (FIG. 4).

In general, within about three seconds following the commencement of the electrosurgical cutting procedure with either the precursor electrodes or the capture component, heat released, for instance, from the steam as steam condensation, consequent latent heat of vaporization within the transfer channel 246 will elevate the temperature of the external surface of the wall of cannula component 32 to excessive levels. Returning to FIG. 5, this surface heat phenomena is seen to be accommodated for through utilization of the insulative sheath represented generally at 120. In the preferred embodiment illustrated in the figure, the sheath 120 is configured as a stainless steel tube or cylinder 270 having a forward standoff at 272 which is configured by rolling the cylindrical end of tube 270. In similar fashion, a rearward standoff 274 is formed by rolling the opposite end of tube 270. With the arrangement of forward and rearward standoffs 272 and 274, an annular air gap or layer 276 is defined. The figure further reveals that extending over the cannula component assembly is an electrically insulative shrink wrap or shrink tube 278. The polyolefin wrap 278 has a thickness of about 0.003 inch. Note that it extends to a forward terminus at 280 wrapped about tip component 200 and to a position of adjacency (with about 1 cm) with ferrule 30 (FIG. 4).

Figure 10:
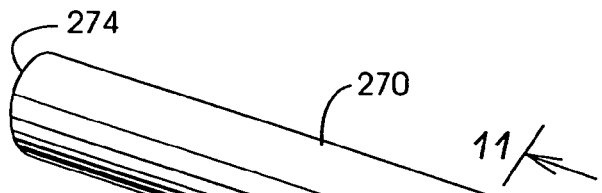
FIG. 10 is a perspective view of a thermal shield according to the invention.
Figure 11:
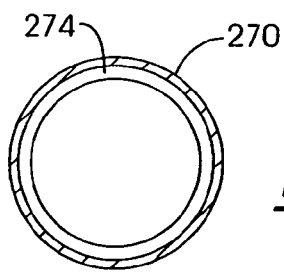
FIG. 11 is a sectional view taken through the plane 11-11 shown in FIG. 10.

Looking momentarily to FIGS. 10 and 11, the thermally insulative sheath or insulative shield tube 270 is revealed in perspective fashion in conjunction with roll formed forward standoff 272. Sectional FIG. 11 illustrates the extent of roll for the rearward standoff 274. In general, the tube 270 is formed of type 304 stainless steel, exhibits a 0.250 inch outer diameter and a wall thickness of 0.006 inch. The "rolled over" standoffs provide about a 0.017 inch annular spacing.

Figure 13:
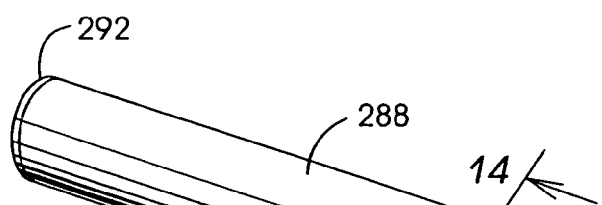
FIG. 13 is a perspective view of another thermal shield according to the invention.
Figure 14:
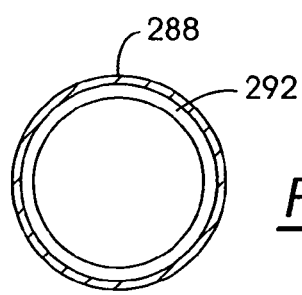
FIG. 14 is a sectional view taken through the plane 14-14 shown in FIG. 13.
Figure 12:
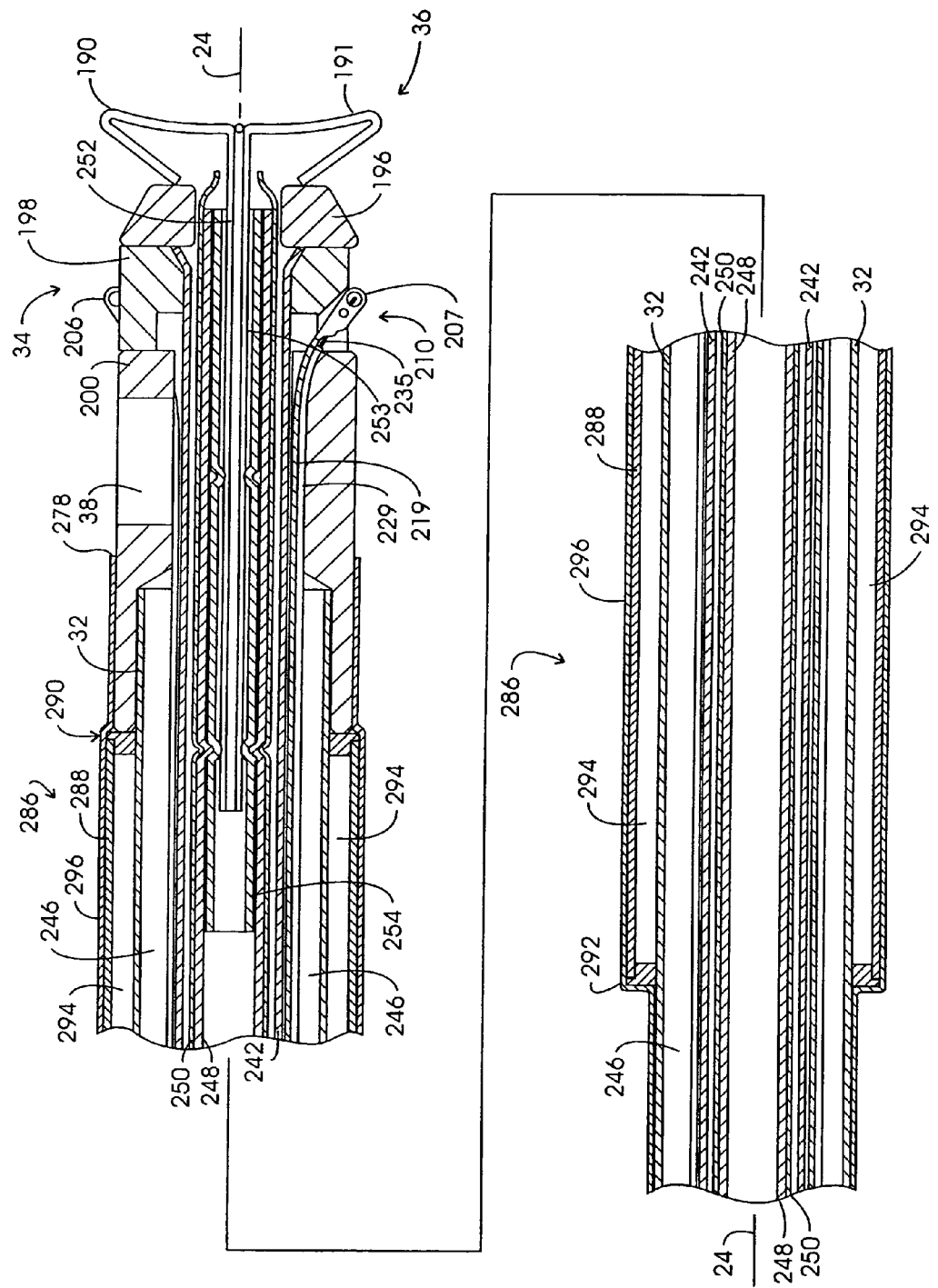
FIG. 12 is a partial sectional view similar to FIG. 5 but showing another embodiment of a thermal shield according to the invention.

Looking to FIGS. 12 through 14, another adaptation of the stainless steel tube implementation of a thermal shield is revealed. With the exception of this thermal shield adaptation, FIG. 12 is identical to FIG. 5. Accordingly, the numerical identification of components as provided in connection with FIG. 5 is imported to FIG. 12 with the exception of the thermal shield structuring and the electrical insulation thereof. The insulator sheath assembly of this embodiment is represented at 286 in FIG. 5. As seen in FIG. 13, the assembly 286 is comprised of an elongate stainless steel tube or cylinder 288. The forward standoff associated with tube 288 is represented in general at 290 and is comprised of a flanged sleeve which may be machined or formed of an injection molded polymer. The rearward standoff 292 is seen additionally in FIG. 14 and is identically structured. Tube 288 reappears in FIG. 12 in combination with forward standoff 290 and rearward standoff 292. Standoffs 290 and 292 serve to provide an annular spacing from the wall of cannula component 32 as represented at annular space 294. As before, the length of the insulator sheath assembly 286 extends essentially from polymeric tip component 200 to a spaced adjacency from ferrule 30 (FIG. 4). Positioned over the tube 288, as before, is an electrically insulative polyolefin shrink wrap or tube 296 which extends from a forward location 298 located over polymeric tip component 200 to adjacency with the rearwardly disposed ferrule 30 (FIG. 4). In general, the tube or cylinder 288 may be formed of type 304 stainless steel; has an outer diameter of 0.250 inch and a wall thickness of 0.006 inch. The shrink wrap 296 will have a thickness of 0.003 inch. As before, the annular air gap 294 has a width of about 0.017 inch to provide air based thermal insulation.

In general, the thermally insulative air gap for the stainless steel thermal shield embodiment will range from about 0.005 inch to about 0.200 inch in extent and the stainless steel cylinders will exhibit thicknesses ranging from about 0.001 inch to about 0.020 inch.

Referring to FIGS. 15 through 17 an extruded plastic implementation for a thermally insulative sheath assembly is depicted. The assembly is identified in general at 300 in connection with FIG. 15. As before, inasmuch as, with the exception of the assembly 300, the components are identical to FIG. 5, the numerical identification thereof is imported from that figure.

Looking additionally to FIGS. 16 and 17, the thermal insulator sheath assembly 300 is configured as an extruded polymeric tube 302 formed of the high temperature resistant semi-crystalline thermoplastic, polyetheretherketone (PEEK), a material exhibiting relatively low thermal conductivity and good mechanical strength at 100° C. Tube 302 is seen to be symmetrically disposed about a tube axis 304 and extends between a forward end 306 and a rearward end 308. Looking to FIG. 15, forward end 306 is seen to be positioned in abutting adjacency with the rearward annular surface of polymeric tip component 200, while the rearward end 308 extends to a location in spaced adjacency from the ferrule 30 (FIG. 4). As before, that distance is selected such that thermal protection is provided against external skin burn or erythema. As is revealed in particular in FIGS. 16 and 17, the internally disposed surface of the cylindrical wall of tube 302 is configured having an array of internally depending rib-form standoffs represented in general at 310. These fourteen rib-form standoffs provide a 0.016 inch minimum annular air gap of thermal insulation over about 80% of the perimeter of the cannula wall 32. The resultant air containing annular spacing is represented in FIG. 15 at 312. As before, the outer surface of tube 302 as well as contiguous components of the cannula component are covered with an electrically insulative polyolefin shrink wrap or shrink tube seen in FIG. 15 at 314 extending from forward location 316 to a location in spaced adjacency from ferrule 30. In general, the thickness from the outer surface of tube 302 to the inwardly depending apecies of the rib array 310 will fall within a range of from about 0.010 inch to about 0.200 inch.

Thermal insulation of the cannula component also can be accomplished employing sufficiently rigid thermally insulative materials such as cross-linked foamed polyethylene marketed by Hitachi Chemical Co. America, Ltd of Cupertino, Calif.; Silicone fiberglass sleeving, or Polyurethane-fiber sleeving, both marketed by CNACC Import & Export Co., Ltd, Zhejiang, China. Other thermally insulative materials include sleeving materials which are air entrained (foamed) such as foamed polyurethane and foamed silicone rubber. In addition low thermal conductivity plastic materials such as urethane and polyimide may be used. Such a thermally insulative sheath assembly is represented generally at 320 in FIG. 18. As before, inasmuch as components other than the sheath 320 are identical to those described in connection with FIG. 5, the numerical identification provided in that figure is imported into FIG. 18. Looking additionally to FIGS. 19 and 20, the assembly 320 is formed with a thermally insulative elongate cylindrical tube 322 extending along a tube axis 324 from a forward end 326 to a rearward end 328. FIG. 18 reveals that the forward end 326 of tube 322 is located in abutting adjacency with the proximal end of polymeric tip component 200 and that the rearward end 328 thereof extends to a location in spaced adjacency with ferrule 30 (FIG. 4). Electrically insulative polyolefin shrink wrap or shrink tubing 328 extends over a portion of polymeric tip component 200 at location 330 and thence over the outer surface of cannula component 32 as seen at rearward location 332. In general, the thermally insulative tube 322 will have a wall thickness of between 0.020 inch to about 0.200 inch. As before, the thickness of the electrically insulative shrink tube layer 328 will be about 0.003 inch.

The extent of caloric involvement associated with interstitially embedded electrosurgical cutting arcs will vary with the size variations of the arc carrying electrode and the duration of arc cutting. For instance, for the capture component structuring described above, where a target tissue volume of about 10 mm maximum diametric extent is involved, the time of the procedure involved for cutting subsequent to precursor electrode energization and positioning will be about seven seconds. Where the maximum diametric extent of the target tissue volume is about 15 mm, then the extent of pursing cable carrying an electrosurgical cutting arc will expand as well as the time interval for completing a capture. That time interval will be about 10 seconds. Correspondingly, where the maximum diametric extent of the target tissue volume is about 20 mm, then the extent of pursing cable play-out to form an electrosurgical cutting arc will expand still further and the time required for completing a capture will increase to about 12 seconds.

Surface heating characteristics of two of the above-described cannula components with associated thermal shields and polyolefin coverings were analyzed utilizing a finite-differencing heat transfer computer program identified as "TRUMP". The TRUMP program was originally authored by the Lawrence Livermore Laboratory, (Los Alamos National Laboratory) and subsequently became available through the Oak Ridge National Laboratory (ORNL). Those cannula structures evaluated are described in conjunctions with FIGS. 5, 10 and 11 (stainless steel with rolled end standoffs) and with FIGS. 15-17 (internally ribbed PEEK shield). These instruments were analyzed in conjunction with their associated thin black (polyolefin) shrink wrap coverings as identified respectively at 278 and 314.

The TRUMP program provides a transient (temporal) analysis where the instrument structure is modeled using parameters having thermal effects. For example, the instruments (probes) are surrounded by room air and may be in partial contact with skin, exhibit mass, material densities, specific heat, thermal conductivity, exhibit air gaps which are open or are combined with ribbing (276-312) will exhibit emittance coefficients such as that of the black shrink wrap (e=0.95), emittance coefficient of stainless steel (e=0.3) and combined or effective emittances. With respect to partial cannula assembly contact, the program-based analysis also accounts for the heat sinking effects envisioned with the black polyolefin covered shield being in contact with exposed skin as discussed in conjunction with FIG. 3.

Figure 21:
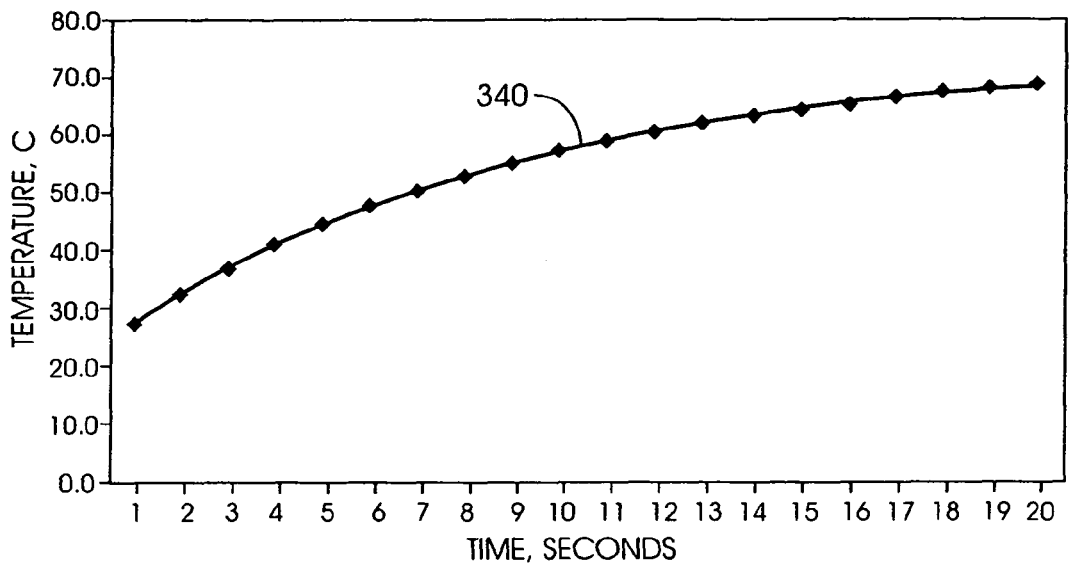
FIG. 21 is a graph plotting temperature versus time illustrating computed thermal shield surface temperatures under room air conditions.
Figure 22:
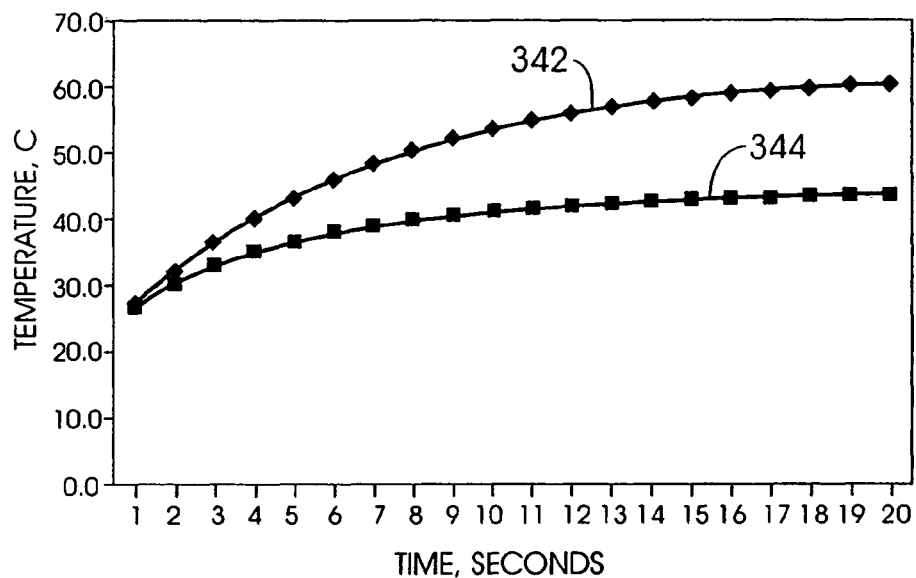
FIG. 22 is a graph plotting computed temperatures for a thermal shield under conditions wherein one half of it is in contact with tissue.

The results of an analysis with respect to the rolled end stainless steel thermal shield structure are revealed in connection with FIGS. 21 and 22. Looking to FIG. 21, curve 340 is seen to relate thermal shield surface temperature with the duration of electrosurgical arc generation and consequent generation of steam. For this analysis, the cannula assembly or probe is considered to be surrounded by room air. Note that the probe surface temperatures range from a level below 30° centigrade at the outset to a level below 70° centigrade at an elapsed interval of 20 seconds. Recall that for a 10 mm capture procedure, the elapsed time will be about 7 seconds at which time the surface temperature of the instrument will be about 50° centigrade. Correspondingly, for a 15 mm diametric capture at about 10 seconds the surface temperature of the instrument will remain below 60° centigrade. Finally, for a 20 mm diametric extent capture and an elapsed interval of about 12 seconds, the computed surface temperature of the instrument will be about 60° centigrade.

Now looking to the conditions described in connection with FIG. 3 and FIG. 22, the computed values of thermal shield surface temperature for the upper half of the device which is exposed to air are represented at curve 342. Correspondingly, where the heat sinking effect of contact with skin is modeled and computed, curve 344 obtains. Note that for a 10 mm diametric extent of capture, at about 7 seconds, the upper temperature of the thermal shield surface will be below 50° centigrade and the temperature of the thermal shield in contact with skin 134 (FIG. 3) will be below 40° centigrade. These values are quite acceptable. For a target tissue volume capture representing a 15 mm target maximum diametric extent and a capture interval of about 10 seconds, the temperature of the thermal shield surface against skin as shown at curve 344 will remain close to 40° centigrade while the opposite non-contacted shield surface as represented at curve 342 will rise between 50 and 60° centigrade. Finally, for a capture involving a target tissue volume of about 20 mm diametric extent, the elapsed capture time will be about 12 seconds. For this condition as shown at curve 344, the temperature at the surface of the thermal shield against skin 134 will remain close to 40° centigrade, while the temperature at the opposite side of the thermal shield exposed to room air as represented at curve 342 will be between 50° centigrade and 60° centigrade.

Figure 23:
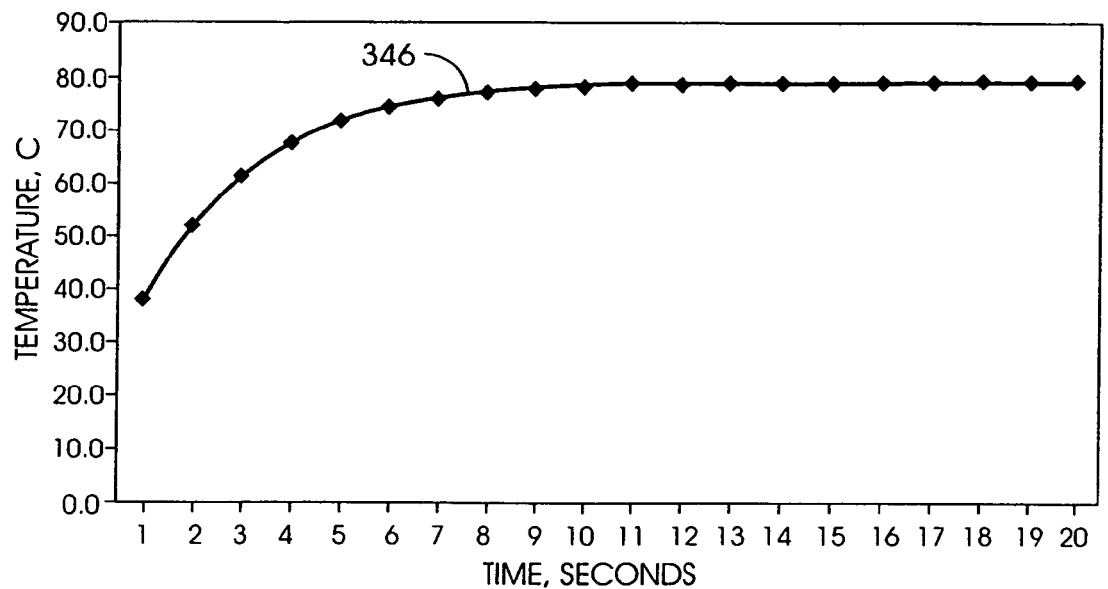
FIG. 23 is a graph plotting the temperature of another thermal shield surface versus time for a room air environment.
Figure 24:
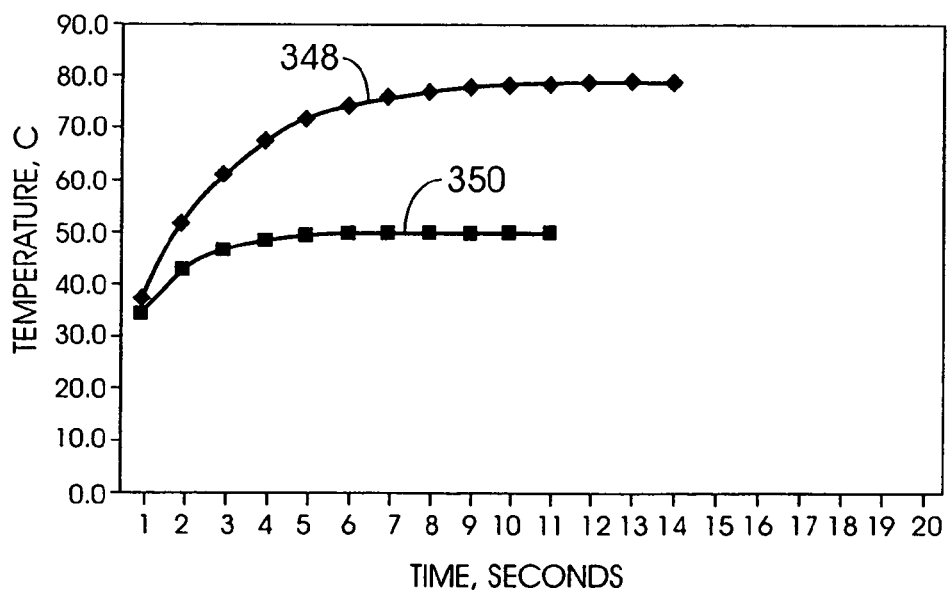
FIG. 24 is a graph plotting computed thermal shield surface temperatures for one half air contact and one half tissue contact.

FIGS. 23 and 24 provide corresponding curves developed by the program in connection with the thermal modeling of the polyetheretherketone (PEEK) internally ribbed thermal shield as described in connection with FIGS. 15-17. For the analysis, a studied assumption was made that the width of the contact between the internally disposed rib peaks and the outer wall of the cannula component 32 was 0.005 inch. It further may be noted that the PEEK material generally exhibits a low thermal conductivity with respect to plastic materials and that the ribbed dimensions employed were at the lower limit of extrudability in terms of their small dimensions. Looking to FIG. 23, curve 346 represents an analysis of the instrument or probe wherein the polyolefin covered thermal shield surface is exposed to room temperature air. The curve reveals, that at the noted 7, 10 and 12 second capture intervals, the thermal shield surface temperature remains above 70° centigrade.

Looking to FIG. 24, conditions as represented at FIG. 3 are plotted. In curve 324 it may be observed that the computed temperatures for the top half of the polyolefin covered thermal shield again are above 70° centigrade at the noted time intervals of 7, 10 and 12 seconds. On the other hand, as represented at curve 350, the surface temperature of the shield bottom half in contact with tissue as at 134 in FIG. 3 remains at about 50° centigrade. For the capture component embodiments, those temperature values represented in FIGS. 23 and 24 are considered to be excessive. However, for instruments engendering lesser caloric activity the extruded polymeric internally ribbed shield may be found to be acceptable. For the instant analysis, the higher surface temperatures at the covered shield may be due to increased thermal conduction. Tracing radially outwardly through the radial center-line of a given rib as illustrated in FIG. 17, the cross-sectional area of the rib will be seen to increase toward the shield outer surface. Thus, thermal resistance decreases, a condition which facilitates the transport of heat from the cannula component 32.

Training involving a simulation of clinical experience with the system 10 is, in part, carried out by prospective practitioners utilizing a breast phantom block or mass which is positioned over a dispersive return electrode. For training purposes, the cannula assembly with excited precursor electrodes then is inserted into this phantom breast to a pre-designated location, whereupon a capture procedure is undertaken. The phantom material is a substantially transparent, jell-like material functioning to emulate the physical and electrical characteristics of the human female breast. The material is marketed under the trade designation "Ultrasonic BP Breast Phantom" by Pharmaceutical Innovations, Inc. of Newark, N.J. In general, the phantom mass exhibits a resistance of about 300 ohms.

Using this phantom breast material, an in vitro study was undertaken to further assess the instrument probe or cannula component surface temperature with and without a thermal shield as described in conjunction with FIGS. 5, 10 and 11. A conventional reusable component or "handle" 14 manufactured by Medsource Technology of Newton, Mass. was employed in conjunction with an evacuation system 52 manufactured by Stackhouse, Inc. (supra) The disposable components or probes 16 were configured for capturing target volumes of 10 mm, 15 mm, and 20 mm maximum diametric extents The evacuation outlet 180 (FIG. 4) exhibited a 3/16 inch internal diameter. Surface temperatures at the cannula assembly (22) or cannula component (32) were measured over an 18 second period commencing with the commencement of a capture mode utilizing a thermocouple fixed to the upper side of the cannula at a position 0.934 inches behind the rearward edge of polymeric tip component 200 (FIG. 5). A strip chart recorder was employed for recording temperature/time information.

Figure 25:
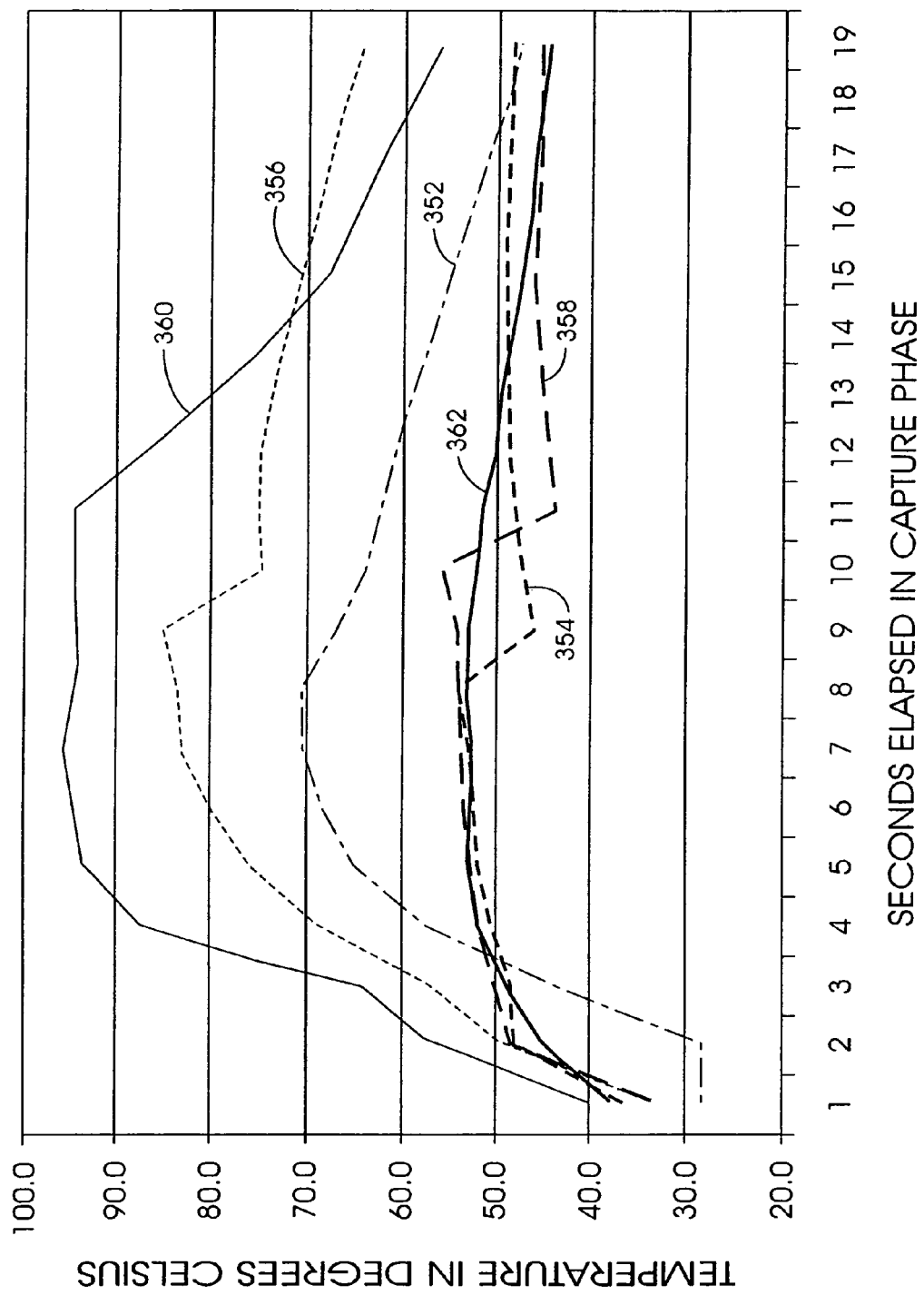
FIG. 25 is a graph plotting instrument cannula surface temperatures for three different capture diameters and with and without thermal shielding.

Referring to FIG. 25 time/temperature data from this in vitro testing are plotted. In this regard, curve 352 presents temperature versus time data for utilization in the test of an instrument without a thermal shield for a capture involving a capture component maximum diametric extent of 10 mm. Note that at the termination of capture or about 7 seconds, the surface temperature at the cannula component exceeded 70° Celsius. However, as represented at curve 354, with the utilization of a stainless steel shield with rolled ends, maximum surface temperatures measured were, as a maximum, slightly above 50° Celsius.

Where the disposable component 16 was configured for capturing a target tissue volume of 15 mm maximum diametric extent and with a configuration wherein no thermal shield was employed, then the surface temperatures represented at curve 356 were encountered. Note that at about 10 seconds or the completion of capture for this configuration, surface temperatures exceeded 80° Celsius. Correspondingly, where the heat shield described in connection with FIG. 5 was employed with the disposable component 16, then surface temperature/time curve 358 was derived. Note that at the completion of capture or about 10 seconds a maximum thermal shield surface temperature encountered was slightly greater than 55° Celsius.

Where the disposable component 16 was configured for capturing target tissue volumes having a maximum diametric extent of 20 mm and no thermal shield was employed, then the results represented at curve 360 were encountered. Capture completion for this test was at the termination of an interval of about 12 seconds and it may be observed that a cannula component surface temperature of greater than 90° Celsius was encountered. However, as represented at curve 362, where the thermal shield represented at FIGS. 5, 10 and 11 was employed, at the conclusion of a 12 second interval, a thermal shield surface temperature of slightly greater than 50° Celsius was witnessed.

Figure 26:
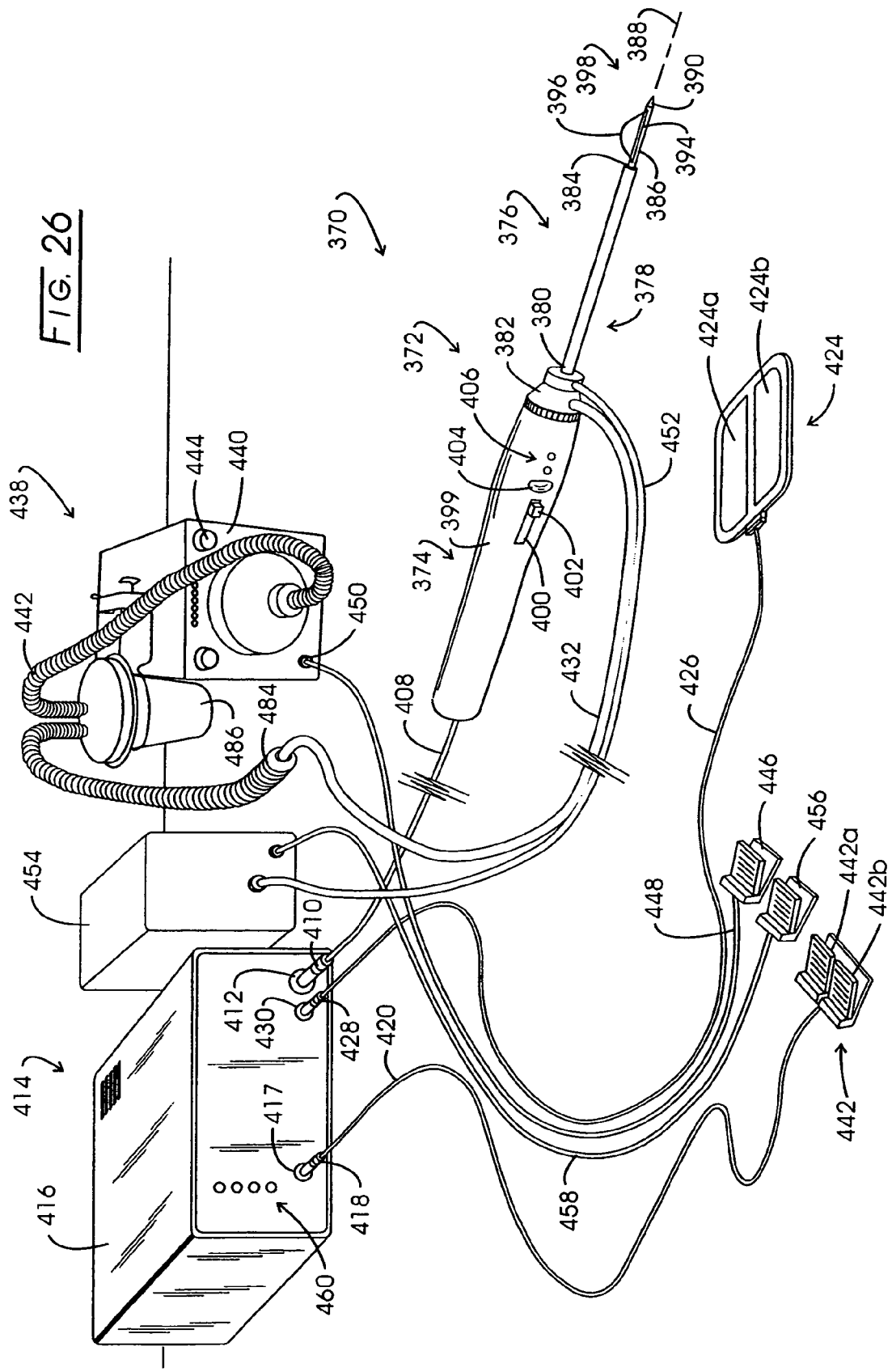
FIG. 26 is a perspective view of another embodiment of a system according to the invention.

Referring to FIG. 26, an electrosurgical target tissue isolation system is portrayed which is configured to carry out a devitalization of a target tissue volume. With such procedures, once electrosurgically circumscribed and isolated from adjacent vascularization the target tissue volume is left in place. A preferred arrangement for such system is described by Eggers in U.S. Pat. No. 6,514,248 (supra) which is incorporated herein by reference. System 370 includes an instrument represented generally at 372 having a handle or reusable component 374 into which a disposable component or probe represented generally at 376 is removably connected. The disposable component 376 is seen having a cannula component and thermal shield assembly represented generally at 378 which, at its proximal end 380 is supported from a manifold 382. The thermal shield of assembly 378 extends to a distal terminus 384, whereupon the cylindrical stainless steel cannula component 386 which it surmounts extends forwardly along an axis 388 to a trocar tip 390. Within the forward region extending rearwardly of tip 390 as at 392 there is formed an elongate deployment slot 394. The figure shows a compressively deployed stainless steel wire-like and arch-shaped electrosurgical cutting electrode 396. The rearward entrance to slot 394 will be seen to function as a suction input port to remove elevated temperature fluid including steam, generated in conjunction with forward region 392. Where the tip 390 is implemented with precursor or positioning electrodes as described above, the positioning elevated temperature fluid encountered during their electrosurgical excitation also will be removed through that suction input port.

Disposable component 376 of instrument 372 is threadably engageable with the handle or reusable component 374 just behind manifold 382. Handle 374 is formed of a polymeric material and includes a polymeric housing having a slot 400 formed therein through which a hand manipulated slidable tab 402 protrudes. The practitioner manually moves this tab 402 forwardly to cause the wire electrode 396 to be compressibly urged against its connection with the forward region of slot 394 to move from a position retracted within the slot to a deployed arch-like orientation as shown. Correspondingly, the electrode is retracted by moving tab 402 rearwardly. Also located upon housing 398 is a button switch 404 manually depressable to cause electrosurgical energy to be applied to the electrode 396. Also shown as being located forwardly of the switch 404 are two LED cueing lights represented generally at 406. Electrical energy for electrosurgical activity is applied to the handle 374 and thence to the cutting electrode 396 via a flexible cable 408 having a cable connector 410 which is inserted within a console connector 412 forming a part of an electrosurgical generator represented generally at 414.

The electrosurgical generator 414 includes a console 416 which, in addition to connector 412, includes a console connector 416 to which is coupled a cable connector 418 and associated control cable 420 extending, in turn, to a footswitch assembly represented generally at 422. Switch assembly 422 includes a footswitch 422a actuable to create a cutting arc at electrode 396 and a footswitch 422b which may be employed, for example, to apply a coagulating electrosurgical current to the electrode.

Electrode 396 performs in a monopolar fashion. Accordingly, a dispersive electrode assembly represented generally at 424 is positioned against the skin of the patient at a location remote from the electrode region of influence. As before, the electrode 424 includes two electrode components 424a and 424b and is connected to a return cable 426 which extends in turn to a cable connector 428. Connector 428 is coupled with console connector 430.

Manifold 382 as well as the cannula component 386 are portions of an evacuation system for removal of elevated temperature fluid. In this regard, the evacuation system includes an inlet port at the entrance of slot 394, a transfer channel formed within the cannula component 386, manifold 382 and an evacuation outlet (not shown) extending from the manifold. Attached to that outlet is a transparent flexible evacuation tube 432 which extends, in turn, to a flexible hose 434. Hose 434 extends to a fluid collection and filtering component 436 of a suction assembly represented generally at 438. Vacuum is applied to the component 436 from a vacuum pump 440 via flexible hose 442. Pump 440 may be activated from a hand switch as at 444. Alternately, the pump 440 may be activated from a footswitch 446 coupled thereto via a cable 448 at a connector assembly 450.

The assembly 378 also provides a second transfer channel feature to the system 370 permitting the expression of a barrier fluid into the cut formed by electrode 396 subsequent to its cutting activity. Such an arrangement is described in the above-noted U.S. Pat. No. 6,514,248. For this purpose, manifold 382 is further formed with a fluid input (not shown) coupled to a flexible delivery tube 452 which extends, in turn, to a barrier fluid reservoir and pump assembly 454. Assembly 454 is activated from a footswitch 456 which is coupled thereto from a cable assembly 458.

Visual cueing is provided to the practitioner at the console 416 as represented at the LED array 460. Such cueing will include, for example, the indication of an actively energized electrode 396 as well as any fault detected by a patient circuit safety monitor (PCSM) check as above-described in connection with the dispersive electrode 424.

Looking to FIG. 27, an enlarged view of the probe 376 is presented. In the figure, the electrode 396 is shown covered with an electrical insulated sheath 466 as it extends through manifold 382 to a rearward tip 468. Tip 468 is engaged with a drive member having the earlier-described tab 402 such that it may be manually urged forwardly to cause electrode 396 to deploy in compression and rearwardly to retract. Seen extending from the manifold 382 is an evacuation outlet 474 connectable with tubing 432 and an input port 488 connectable with tube 452 (FIG. 26). External threads 472 extending from manifold 382 provide for connection with housing 398.

Referring to FIG. 28 forward region 392 is shown in sectional detail. Note that the distal end 462 of electrode 396 is fixed at the tip region by a fitment 464 and extends through the hollow interior of cannula component 386. As it so extends, the electrode 396 is covered with the noted electrically insulative sheath 466. The electrode 396 is somewhat rigid and is caused to deflect or deploy outwardly as shown upon the manual assertion of compressive force from tab 402 (FIG. 26) against its rearwardly disposed end at 468. Electrode 396 is retracted by a reverse maneuver. Note that the electrode wire with sheath 466 extends through a seal 470 mounted within manifold 382. Looking to that manifold, the rearward portion thereof is shown carrying the noted externally disposed threads 472 which engage corresponding internal threads within the forward portion of housing 398. Manifold 382 additionally is shown having an integrally formed evacuation outlet 474 which is in vacuum and fluid communication with the interior cavity and transfer channel 476 within cannula component 386. This transfer channel 476 extends forwardly to the rearward portion of deployment slot 394 to define an intake port located at the arrow 78.

Electrode 396 may be formed, for example, of type 304 stainless steel titanium or the like. In general, the electrode 396 will have a diameter within a range of from about 0.1 mm to about 1.0 mm and the cannula component 386 will have a diameter ranging from about 1 mm to about 5 mm. To facilitate deployment of the electrode 396 in the arch-shape shown, a deflector guide component 480 may be positioned within the slot 394. Because the entire instrument 372 (FIG. 26) is rotated as part of a circumscription procedure the sides of slot 394 form an abutment supporting the outward deployment of electrode 396.

The thermal shield component of assembly 378 is represented at 482. Shield 482 may assume a variety of configurations including the extruded polymeric design described in connection with FIGS. 15-17. In the latter regard, the extent of thermal energy expended in a procedure with the smaller electrode configuration 396 permits such utilization. With the instant arrangement, however, the thermal shield provides a second interior channel 484 having, for example, an output port represented at arrows 486. Port 486 extends in fluid communication with the input port 488 formed within manifold 382. Port 488 is connectable, as noted above, with tubing 452 to provide for the expression of barrier fluid via the output port represented at arrows 486. Alternately, the port 388 may be left open to atmosphere and will thus provide a return flow with respect to suction applied via evacuation outlet 474.

Looking to FIG. 29, the interior structure of assembly 378 is revealed. Thermal shield 482 is shown to be formed of the earlier-described PEEK thermoplastic material. The shield is configured with an interiorly disposed array of ribs represented generally at 490 which extend along in parallel with the axis 388 (FIG. 26) of the probe 376. The arrayed ribs at 490 perform as standoffs to define the channel 484 which provides insulation by virtue of an air layer, as well as a channel for delivery of barrier fluid.

Reusable handles similar to that shown at 374 in FIG. 26 may be employed to support a variety of electrosurgical cutting instruments incorporating thermal shielding as well as evacuation systems for removing steam, smoke and fluids such as blood and/or pooled local anesthetic. Such a disposable electrosurgical probe is illustrated in connection with FIGS. 30 and 31. Looking to FIG. 30, the disposable probe component is represented generally at 500. Probe 500 is configured with a tubular thermally insulative cannula assembly 502 extending about an instrument axis 504 from a forward region 506 to a proximal or rearward region 508 which is fixed to a manifold 510. Manifold 510 is configured substantially similarly to manifold 382 (FIG. 28) but incorporates a singular evacuation outlet 512. Outlet 512 is configured for attachment with evacuation or suction tubing as described at 432 in FIG. 26. Connection of the manifold 510 to a reusable handle or the like similar to that shown at 374 is with externally disposed threads 514.

Looking additionally to FIG. 31, cannula 502 is seen to be, in and of itself, a thermal insulator similar to that described at 322 in FIGS. 18-20. FIG. 31 reveals the presence of a transfer channel 516. That channel 516 extends in suction communication with evacuation outlet 512 of manifold 510. For the instant embodiment, the forward region 506 of cannula 502 is seen to support an electrically insulative and heat resistive generally cylindrically shaped electrode support member 518. Member 518, in turn, is configured having a cylindrical wall 520 within which is embedded a generally U-shaped electrosurgical electrode 522. Note, however, that wall 520 is disposed about a cylindrical passage 524 having an input opening 526. Accordingly, the passage 524 is in suction and fluid communication with the transfer channel 516. Support member 518 may be configured with an electrically insulating and temperature resistant material, for example, a ceramic such as alumina or a high temperature resistive plastic such as Teflon (polytetrafluoroethylene). One tine of electrode 522 is seen electrically coupled with an electrical lead 528 which, in turn, is electrically insulated by an electrically insulative polymeric sheath 530. The combined sheath 530 and lead 528 extend rearwardly from the manifold 510 for ultimate connection within the handle to an electrosurgical generator in fashion similar to that described in connection with FIG. 26. Electrode 522 may be formed of type 304 stainless steel, tungsten or titanium and will have a diameter from about 0.1 mm to about 1 mm. In general, the spacing between the two tines of electrode 522 will range from about 1.0 mm to about 5 mm and the loop component defined by these tines of the electrode 522 will extend from the forward surface of support member 518 a distance from about 0.2 mm to about 20 mm. In general, the outer diameter of the combined thermal insulator and cannula 502 will fall within a range from about 3 mm to about 10 mm. The cylindrical structure will exhibit a wall thickness of from about 0.3 mm to about 3 mm.

The disposable probe structure 500 may be provided with a different tip structuring. Such an arrangement is revealed in FIGS. 32 and 33. Looking to FIG. 32, the disposable probe is shown in general at 540 having a thermally insulative cannula assembly 542 structured identically as cannula 502. Cannula 542 extends along an axis 544 from a forward region 546 to a proximal or rearward region 548, whereupon it is supported by a manifold 550. As before, manifold 550 is configured having an evacuation outlet 552 in fluid and suction communication with a transfer channel within cannula 542 and connectable with the suction tubing of an evacuation system such as that described in connection with FIG. 26. Removable connection of the manifold 550 to a reusable instrument handle, for example, similar to that shown at 374 in FIG. 26 is by external threads seen at 554.

Looking additionally to FIG. 33, the wall of cylindrical or tubular cannula 542 is seen to surmount an internal cavity functioning as a transfer channel 556. Channel 556 is in fluid and suction communication with evacuation outlet 552 of manifold 550. Mounted within the channel 556 at tip region 546 is an electrically and thermally insulative cylindrical support member 558. As before, member 558 may be formed of a heat resistant ceramic such as alumina or a high temperature plastic such as Teflon (polytetrafluoroethylene). For the instant embodiment however, the support 558 is somewhat solid such that it will support a thin rod-like electrosurgical electrode 560. Two intake ports as at 562 and 564 are formed as passages extending through support member 558. Ports 562 and 564 are in suction and fluid transfer communication with transfer channel 556. As before, the electrode 560 is connectable with an electrosurgical generator via an electrical lead 566 which extends through the transfer channel 556. In this regard, as before, the lead 566 is surmounted by an electrically insulative polymeric sheath 568 and extends with sheath 568 through manifold 550 (FIG. 32). Electrode 560 may be formed of a type 304 stainless steel, titanium or tungsten and will exhibit a diameter within a range extending from about 0.1 mm to about 2 mm. As before, the ports 562 and 564 are positioned to evacuate steam, smoke and fluids such as blood and accumulations of local anesthetic which may be encountered in the course of a procedure. In similar fashion as cannula 502, cannula 542 may be fabricated as described in connection with the shield structure of FIGS. 18-20.

Another disposable probe configuration which may be employed with the system described in FIG. 26 including variations of the reusable handle component 374 is revealed in FIGS. 34 and 35. Referring to FIG. 34, a disposable probe component is represented generally at 570. Probe 570 includes an elongate rigid thermally insulative tubular cannula 572 which extends along an axis 574 from a forward region 576 to a rearward or proximal region 578. Cannula 572 is supported at region 578 by a manifold 580 which is configured, as before having an evacuation outlet 582. The probe 570 is connected to a handle similar to that described in connection with FIG. 26 by external threads 584.

Looking additionally to FIG. 35, the thermally insulative cannula 572 is configured having an internally disposed transfer channel 586 which is in fluid and suction communication with manifold 580 and evacuation outlet 582 in the same fashion as probes 500 and 540 described above. For the present embodiment, however, the forward region 576 of cannula 572 supports a cylindrically-shaped electrically insulating support member 588. As before, the support member 588 may be formed of a ceramic such as alumina or high temperature plastic such as Teflon (polytetrafluoroethylene). The internal passage or opening of cylindrical support 588, in turn, supports a cylindrical electrode 590. Cylindrical electrode 590 is formed as a tube having a passageway 592 passing therethrough which is symmetrically disposed about a cylinder axis 594. Passageway 592 extends forwardly to define a port 596 at the electrode itself. Electrode 590 may, as before, be formed of type 304 stainless steel titanium or tungsten. The electrode is coupled with an electrical lead 598 which extends through transfer channel 586 and is covered by a polymeric electrically insulative sheath 600. This combination of electrical lead and sheath 600 extends rearwardly from manifold 580 for connection through an associated reusable handle with an electrosurgical generator in the general manner of FIG. 36. Cannula 572 may be formed of material as described in connection with the sheath structure shown in FIGS. 18-20. With the structuring shown, as the electrode 590 is excited with cutting arc forming cutting energy the evacuation system will be in operation removing encountered smoke, steam and fluid. Cylindrical electrode 590 will have an outer diameter within a range extending from about 0.5 mm to about 10 mm. Correspondingly, support member 588 will have an outer diameter in a range of about 1 mm to about 15 mm. The above-described probe cannula components 378, 502, 542 and 572 will have lengths within a range of from about 10 cm to about 50 cm.

Since certain changes may be made in the above system, method and apparatus without departing from the scope of the invention herein involved, it is intended that all matter contained in the above description or shown in the accompanying drawings shall be interpreted as illustrative and not in a limiting sense.

The invention claimed is:

1. The method for carrying out an electrosurgical cutting procedure at the subcutaneous situs of a target tissue volume of given size situate within healthy tissue, comprising the steps of:
   (a) providing an electrosurgical probe having a cannula component with a wall having an outward surface and extending along a probe axis from a supportable proximal end to a working end region having an electrosurgically energizable cutting assembly, said step (a) provides said electrosurgical probe as further comprising an insulator sheath extending substantially over said cannula component wall and spaced an insulation distance from said wall outward surface an extent effective to define a space-based insulative tissue contacting surface exhibiting a surface temperature atraumatic to said healthy tissue;
   (b) providing an evacuation system having an intake port located at said working end region and having a transfer channel extending along and within said cannula component to an evacuation outlet;
   (c) interstitially positioning said electrosurgical probe working end region in an operative orientation with respect to said target tissue volume effective to carry out said procedure;
   (d) energizing said cutting assembly to effect formation of a cutting arc;
   (e) carrying out said procedure by maneuvering said energized cutting assembly, said arc evoking elevated temperature fluid; and
   (f) removing at least a portion of said elevated temperature fluid through said evacuation system intake port and said transfer channel to an extent effective to avoid substantial thermal damage to said healthy tissue.

2. The method of claim 1 in which:
   said step (a) provides said cannula component as comprising an elongate rigid tube, and provides said insulator sheath as a tube extending between a forward stand-off in contact with said cannula component wall outer surface adjacent said working end region and a rearward stand off adjacent said proximal end, said forward and rearward stand-offs being dimensioned to establish said insulation distance.

3. The method of claim 2 in which:
   said step (a) provides said insulator sheath as a cylindrical tube and provides said forward and rearward stand-offs by inwardly rolling the ends of said insulator sheath cylindrical tube.

4. The method of claim 2 in which:
   said step (a) provides said forward and rearward stand-offs as respective forward and rearward inserts mounted intermediate said insulator sheath cylinder and said cannula component outer surface.

5. The method of claim 1 in which:
   said step (a) provides said cannula component as comprising an elongate rigid tube, and provides said insulator sheath as a polymeric tube extending along a tube axis between a forward end adjacent said cannula component working end and a rearward end adjacent said proximal end and having an array of internally depending rib-form stand-offs aligned in parallel with said tube axis and extending into contact with said cannula-component outward surface, said rib-form stand-offs being radially dimensioned to establish said insulation distance.

6. The method of claim 1 in which:

said step (a) provides said electrosurgical probe electrosurgically energizable cutting assembly as further comprising at least one electrosurgically energizable precursor electrode forwardly disposed at said cannula component working end region, said step (a) further provides said cutting assembly as comprising a tissue retrieval capture component positioned within said cannula component working end region, having a forward portion extending to a forwardly disposed cutting electrode assembly energizable to provide a said electrosurgical cutting arc at a supporting leading edge, said capture component being actuable to cause said leading edge to extend from said working end region forwardly toward a maximum peripheral extent corresponding with said target tissue volume given size and subsequently extendable while being drawn toward said probe axis to a capture orientation;

said step (d) energizes said precursor electrode at the commencement of said procedure to effect formation of a precursor cutting arc, said step (d) further energizes said capture component cutting electrode assembly subsequent to said step (c);

said step (c) for interstitially positioning said electrosurgical probe is carried out while said step (d) effects said precursor electrode energization with an attendant generation of positioning elevated temperature fluid;

said step (e) actuates said capture component subsequent to said step (d); and said step (f) carries out removal of said positioning elevated temperature fluid while said precursor electrode is electrosurgically energized, and said step (f) further carries out removal of said elevated temperature fluid while said capture component is actuated.

7. The method of claim 6 further comprising the steps:

(g) removing said cannula component with said capture component in said capture orientation from adjacent said healthy tissue; and (h) continuing the said step (f) removal of said elevated temperature fluid during the carrying out of said step (g).

* * * * *